US009072472B2

(12) United States Patent
Potter et al.

(10) Patent No.: US 9,072,472 B2
(45) Date of Patent: Jul. 7, 2015

(54) DISPOSABLE ASSEMBLY CONTAINING A SKIN PIERCING ELEMENT

(75) Inventors: Charles David Ogilvy Potter, Standlake (GB); David Stuart Potter, Cowes (GB); Graeme Paterson, Cheddar (GB)

(73) Assignee: GLIDE PHARMACEUTICAL TECHNOLOGIES LIMITED, Abingdon, Oxfordshire (GB)

( * ) Notice: Subject to any disclaimer, the term of this patent is extended or adjusted under 35 U.S.C. 154(b) by 1219 days.

(21) Appl. No.: 11/883,901

(22) PCT Filed: Feb. 7, 2006

(86) PCT No.: PCT/GB2006/000411
§ 371 (c)(1),
(2), (4) Date: Apr. 2, 2008

(87) PCT Pub. No.: WO2006/082439
PCT Pub. Date: Aug. 10, 2006

(65) Prior Publication Data
US 2009/0030442 A1    Jan. 29, 2009

(30) Foreign Application Priority Data
Feb. 7, 2005 (GB) .................................. 0502840.2

(51) Int. Cl.
| A61B 17/14 | (2006.01) |
| A61B 5/15 | (2006.01) |
| A61B 5/151 | (2006.01) |
| A61B 5/00 | (2006.01) |
| A61M 37/00 | (2006.01) |
(Continued)

(52) U.S. Cl.
CPC ........... *A61B 5/1411* (2013.01); *A61B 5/15186* (2013.01); *A61B 2019/4873* (2013.01); *A61B 5/150916* (2013.01); *A61B 5/15142* (2013.01); *A61B 5/411* (2013.01); *A61M 5/158* (2013.01); *A61M 37/0069* (2013.01); *A61M 2005/1585* (2013.01)

(58) Field of Classification Search
CPC ............. A61B 5/1411; A61B 5/15186; A61B 5/15142; A61B 17/32093; A61B 5/151; A61B 2019/4873; A61M 5/322; A61M 5/5013
USPC .................. 606/181, 182, 183; 600/573, 583; 604/110, 136, 137–139
See application file for complete search history.

(56) References Cited

U.S. PATENT DOCUMENTS

| 1,819,415 A | 8/1931 | Harris |
| 2,398,544 A | 4/1946 | Lockhart |
| 2,752,918 A | 7/1956 | Uytenbogaart |

(Continued)

FOREIGN PATENT DOCUMENTS

| CA | 1019638 | 10/1977 |
| DE | 3644984 | 7/1988 |

(Continued)

*Primary Examiner* — Jonathan W Miles
(74) *Attorney, Agent, or Firm* — Nixon & Vanderhye P.C.

(57) ABSTRACT

The invention relates to devices used in the fields of drag delivery or sampling. More particularly, it relates to a disposable assembly which is fitted to an actuator device which causes the skin piercing element to enter the skin to deliver a drug (or other substance) or take a sample. Preferably the assembly is "made safe" after actuation, such that the disposable assembly can't be reused and more preferably still the skin piercing element is safely housed in the assembly such that it does not constitute a "sharps" risk.

33 Claims, 26 Drawing Sheets

(51) Int. Cl.
*A61B 19/00* (2006.01)
*A61M 5/158* (2006.01)

(56) References Cited

U.S. PATENT DOCUMENTS

| | | | |
|---|---|---|---|
| 3,616,758 A | 11/1971 | Komarov | |
| 3,901,158 A | 8/1975 | Ferb | |
| 3,948,263 A | 4/1976 | Drake | |
| 3,982,536 A | 9/1976 | Krogseng et al. | |
| 4,059,107 A | 11/1977 | Iriguchi et al. | |
| 4,116,196 A | 9/1978 | Kaplan et al. | |
| 4,326,524 A | 4/1982 | Drake | |
| 4,419,936 A | 12/1983 | Coates et al. | |
| 4,449,982 A | 5/1984 | Gould, III | |
| 4,518,387 A | 5/1985 | Murphy et al. | |
| 4,664,664 A | 5/1987 | Drake, Jr. | |
| 4,790,824 A | 12/1988 | Morrow et al. | |
| 4,808,184 A | 2/1989 | Tepic | |
| 4,863,429 A | 9/1989 | Baldwin | |
| 4,871,094 A | 10/1989 | Clements et al. | |
| 4,968,302 A | 11/1990 | Schluter et al. | |
| 5,092,842 A | 3/1992 | Bechtold et al. | |
| 5,116,313 A | 5/1992 | McGregor | |
| 5,206,024 A | 4/1993 | Peery et al. | |
| 5,354,287 A | 10/1994 | Wacks | |
| 5,360,410 A | 11/1994 | Wacks | |
| 5,542,920 A | 8/1996 | Cherif Cheikh | |
| 5,549,560 A | 8/1996 | Van de Wijdeven | |
| 5,589,167 A | 12/1996 | Cleland et al. | |
| 5,599,302 A | 2/1997 | Lilley et al. | |
| 5,747,058 A | 5/1998 | Tipton et al. | |
| 6,001,385 A | 12/1999 | Van de Wijdeven | |
| 6,102,896 A | 8/2000 | Roser | |
| 6,117,443 A | 9/2000 | Cherif-Cheikh | |
| 6,120,786 A | 9/2000 | Cherif Cheikh | |
| 6,203,521 B1 | 3/2001 | Menne et al. | |
| 6,264,629 B1 | 7/2001 | Landau | |
| 6,331,310 B1 | 12/2001 | Roser et al. | |
| 6,375,971 B1 | 4/2002 | Hansen | |
| 6,586,006 B2 | 7/2003 | Roser et al. | |
| 6,641,555 B1 * | 11/2003 | Botich et al. | 604/110 |
| 6,680,692 B2 | 1/2004 | Solbach | |
| 6,689,093 B2 | 2/2004 | Landau | |
| 6,764,496 B2 * | 7/2004 | Schraga | 606/182 |
| 6,783,509 B1 | 8/2004 | Landau et al. | |
| 2004/0248892 A1 | 12/2004 | Wang | |
| 2006/0161111 A1 | 7/2006 | Potter | |

FOREIGN PATENT DOCUMENTS

| | | |
|---|---|---|
| DE | 3839287 | 5/1990 |
| EP | 0008636 | 3/1980 |
| EP | 0119286 | 9/1984 |
| EP | 0139286 | 2/1985 |
| EP | 0276158 | 7/1988 |
| EP | 0409365 | 1/1991 |
| EP | 0427457 | 5/1991 |
| EP | 0518561 | 12/1992 |
| EP | 0595508 | 5/1994 |
| EP | 0666084 | 8/1995 |
| EP | 0879609 | 11/1998 |
| FR | 1014881 | 8/1952 |
| FR | 1049564 | 12/1953 |
| FR | 2627698 | 9/1989 |
| FR | 2749764 | 12/1997 |
| GB | 993309 | 6/1965 |
| GB | 2193644 | 2/1988 |
| GB | 2239180 | 6/1991 |
| WO | WO 9407553 | 4/1994 |
| WO | WO 9422423 | 10/1994 |
| WO | WO 9640351 | 12/1996 |
| WO | WO 0062734 | 10/2000 |
| WO | WO 0248654 | 6/2002 |
| WO | WO 2003/023773 A1 | 3/2003 |
| WO | WO 2004/014468 A1 | 2/2004 |
| WO | WO 2006082439 | 8/2006 |

* cited by examiner

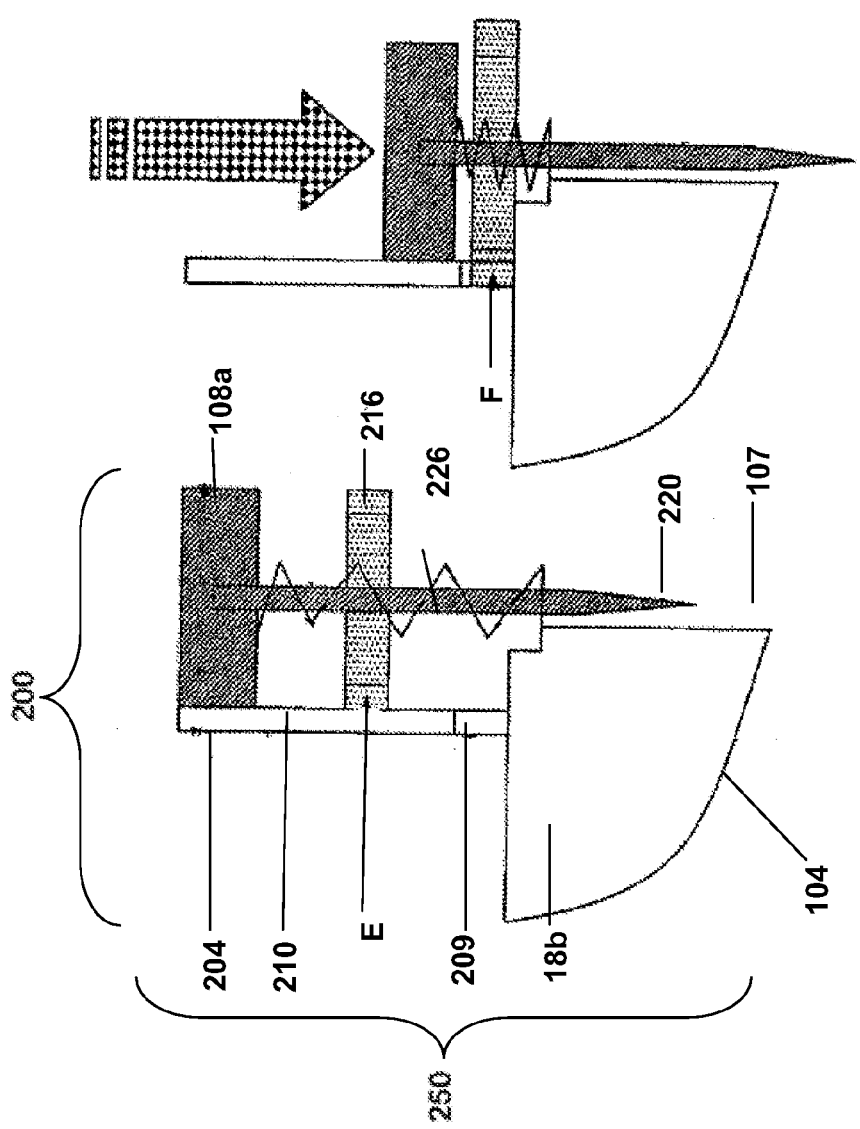

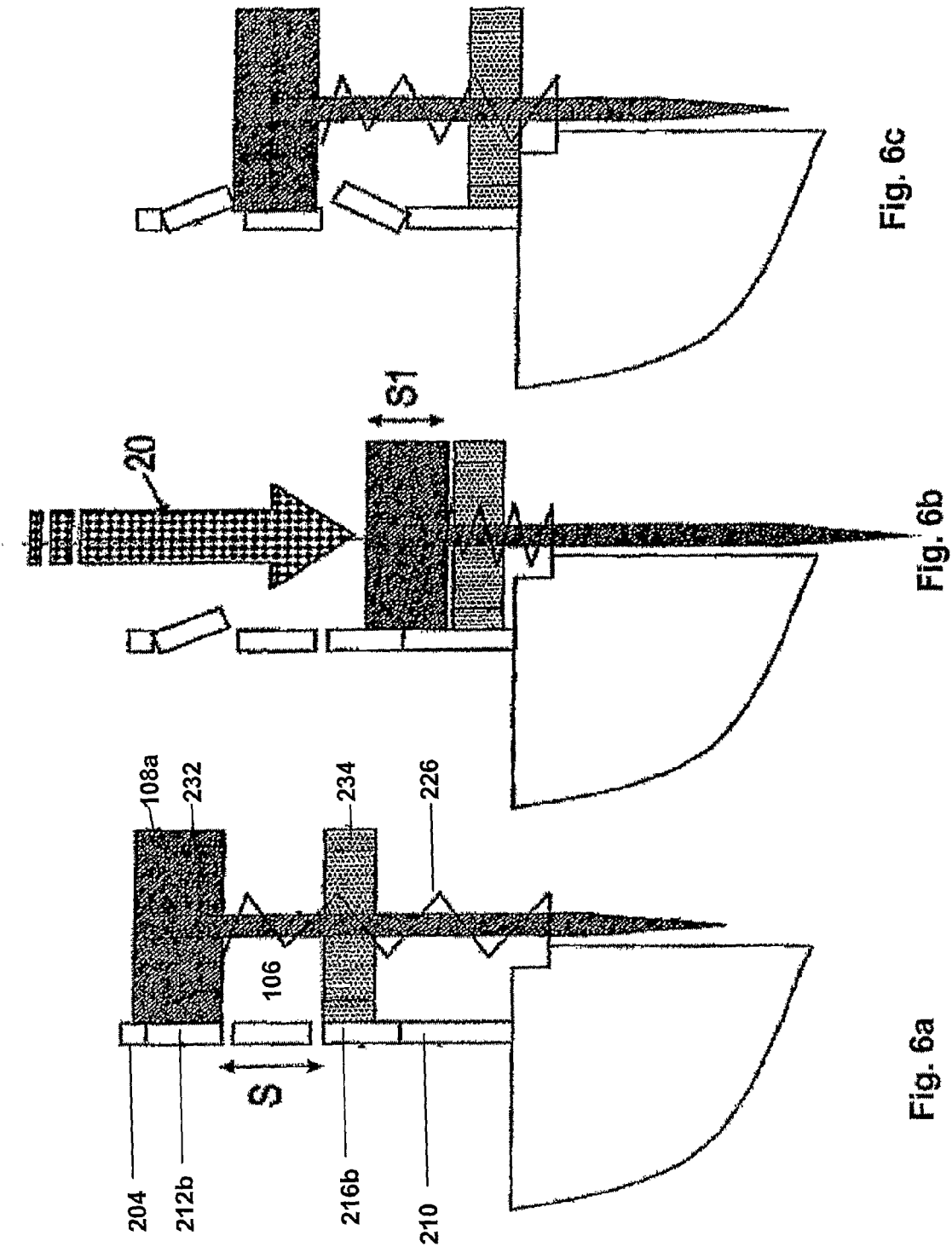

Fig. 7a
Fig. 7b
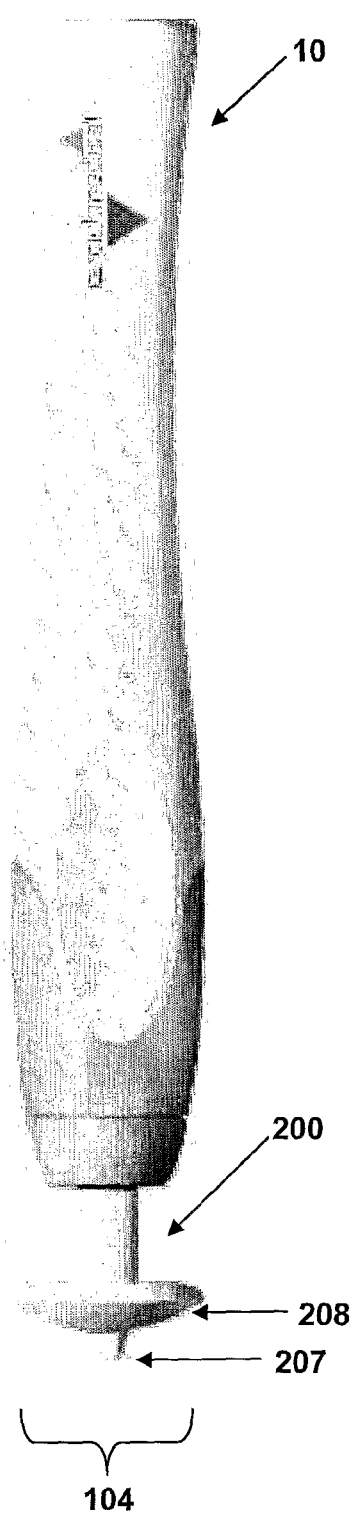
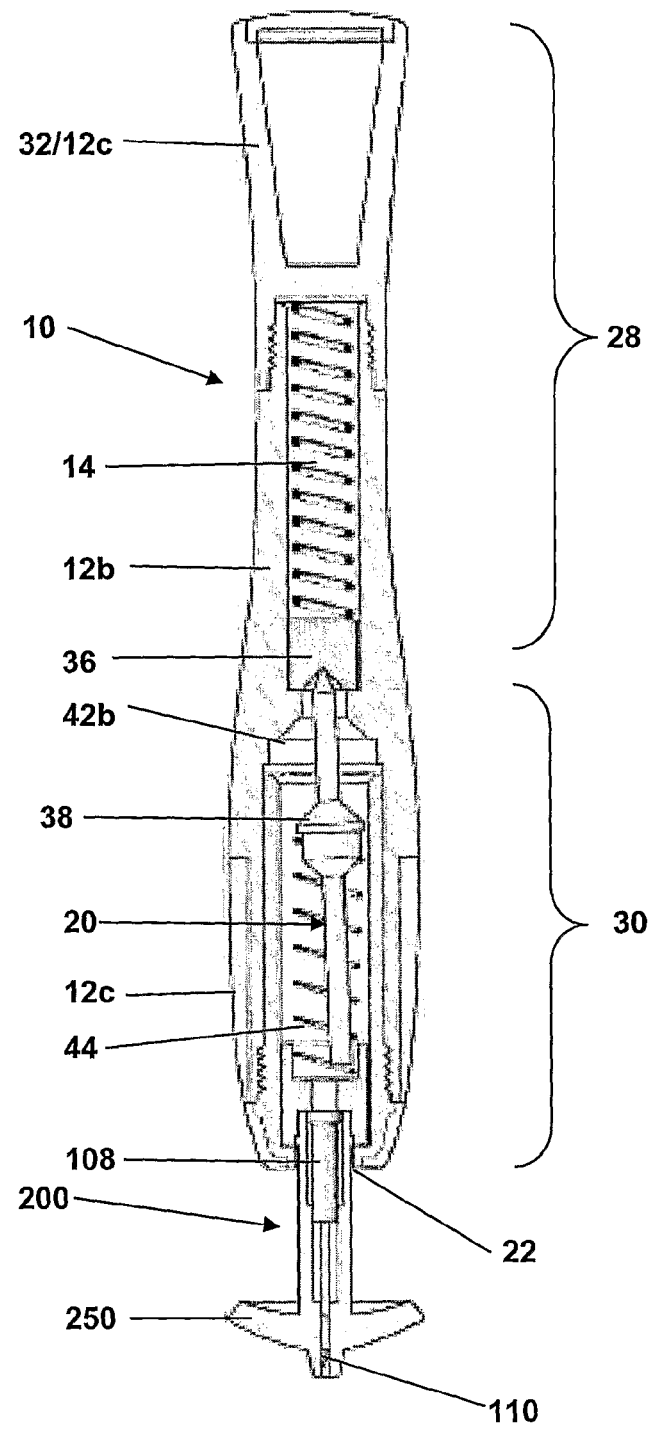

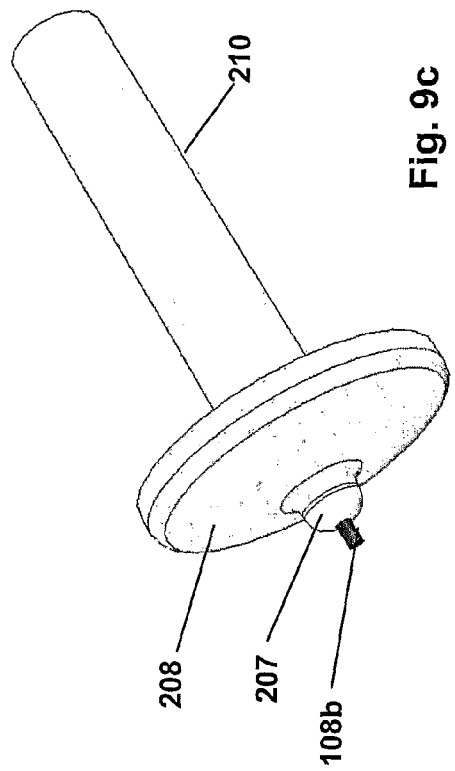
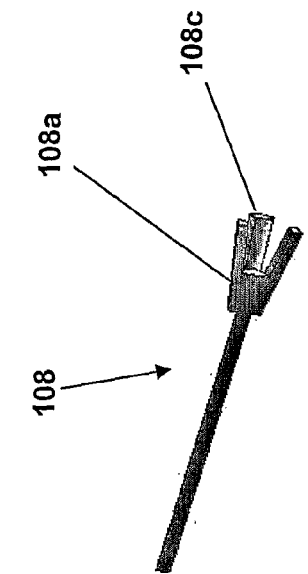
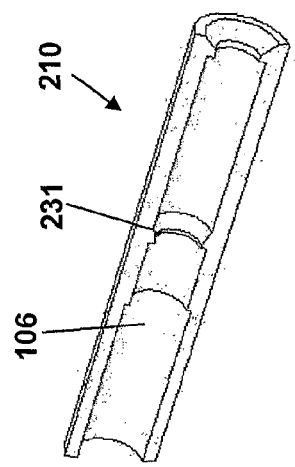
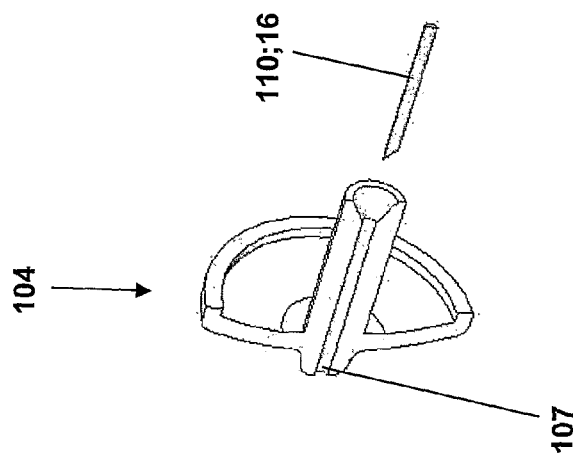
Fig. 9c
Fig. 9d

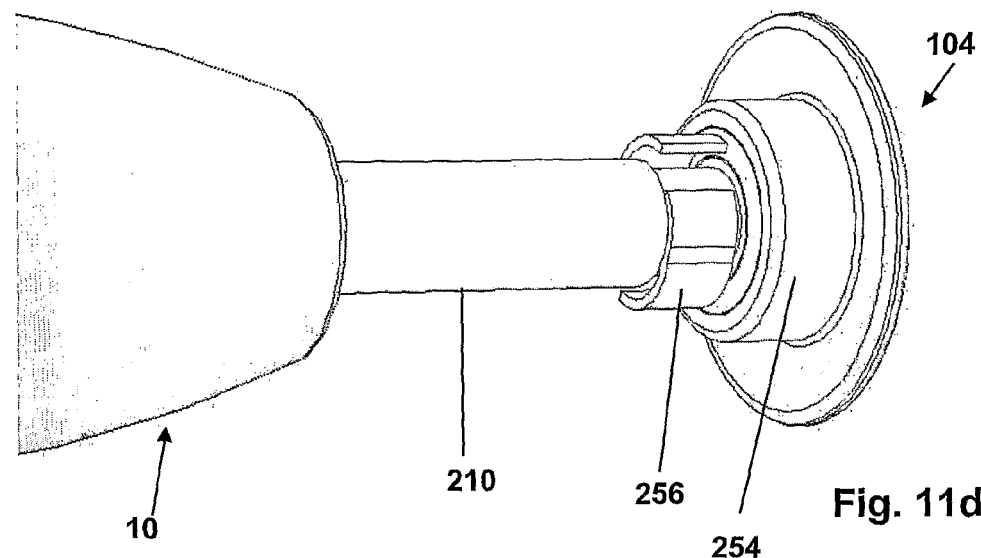
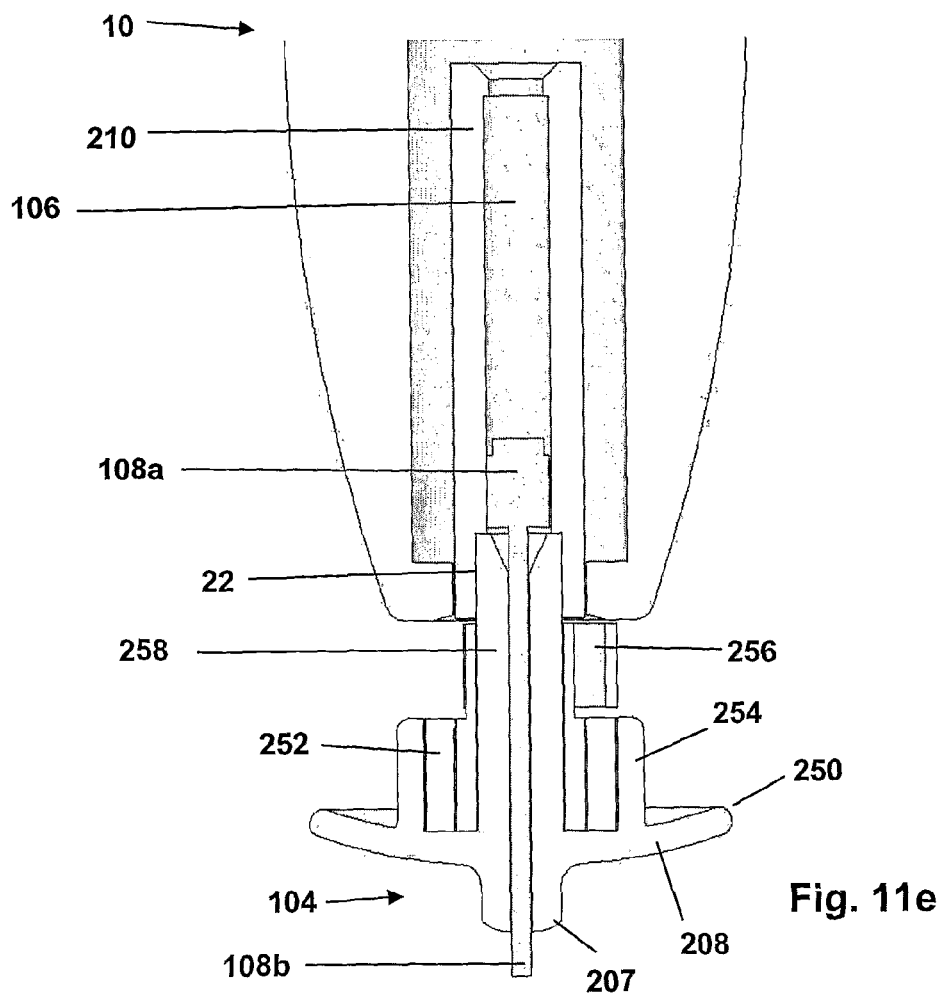

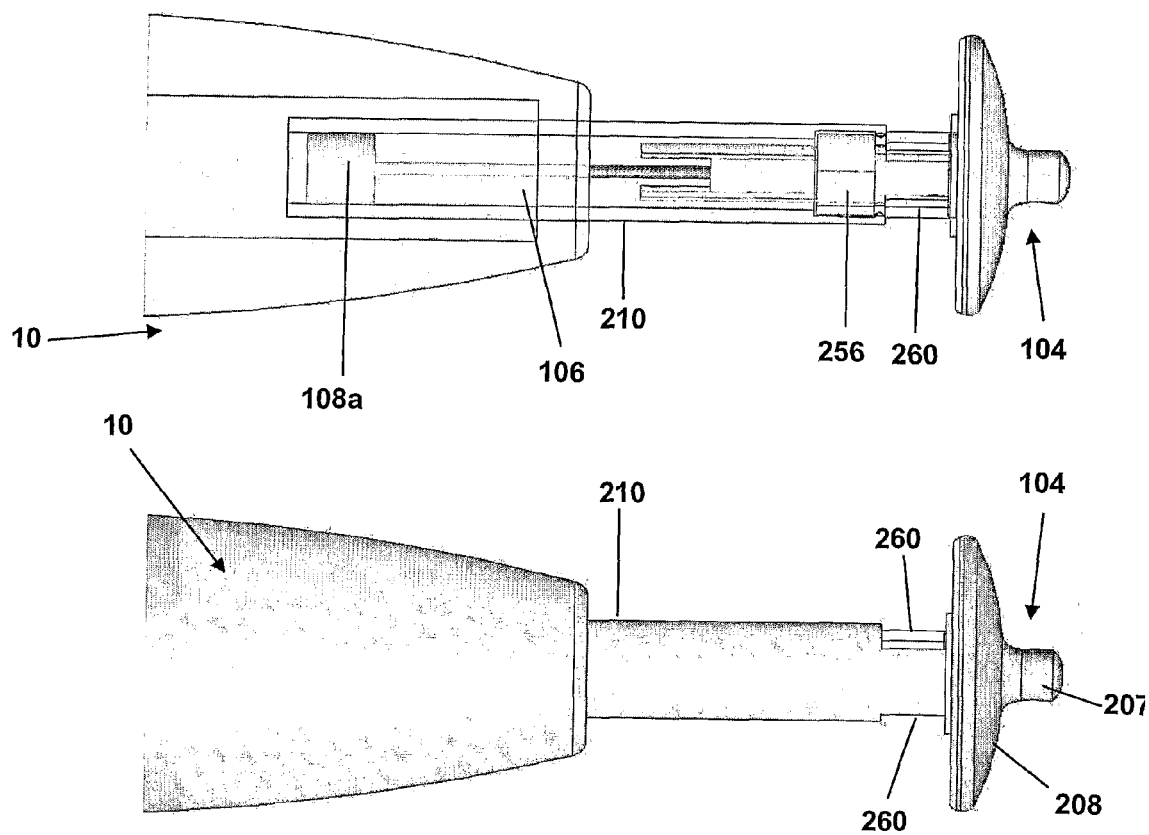
Fig. 12a
Fig. 12b
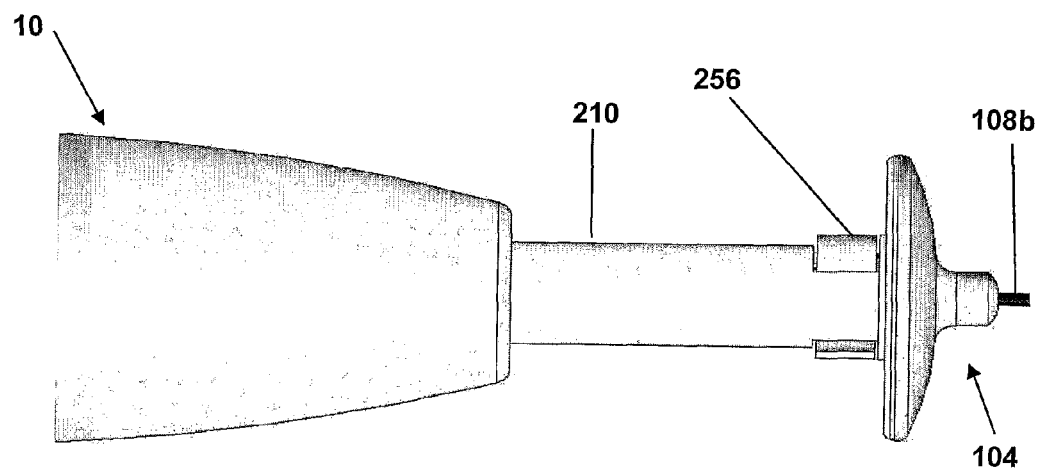
Fig. 12c

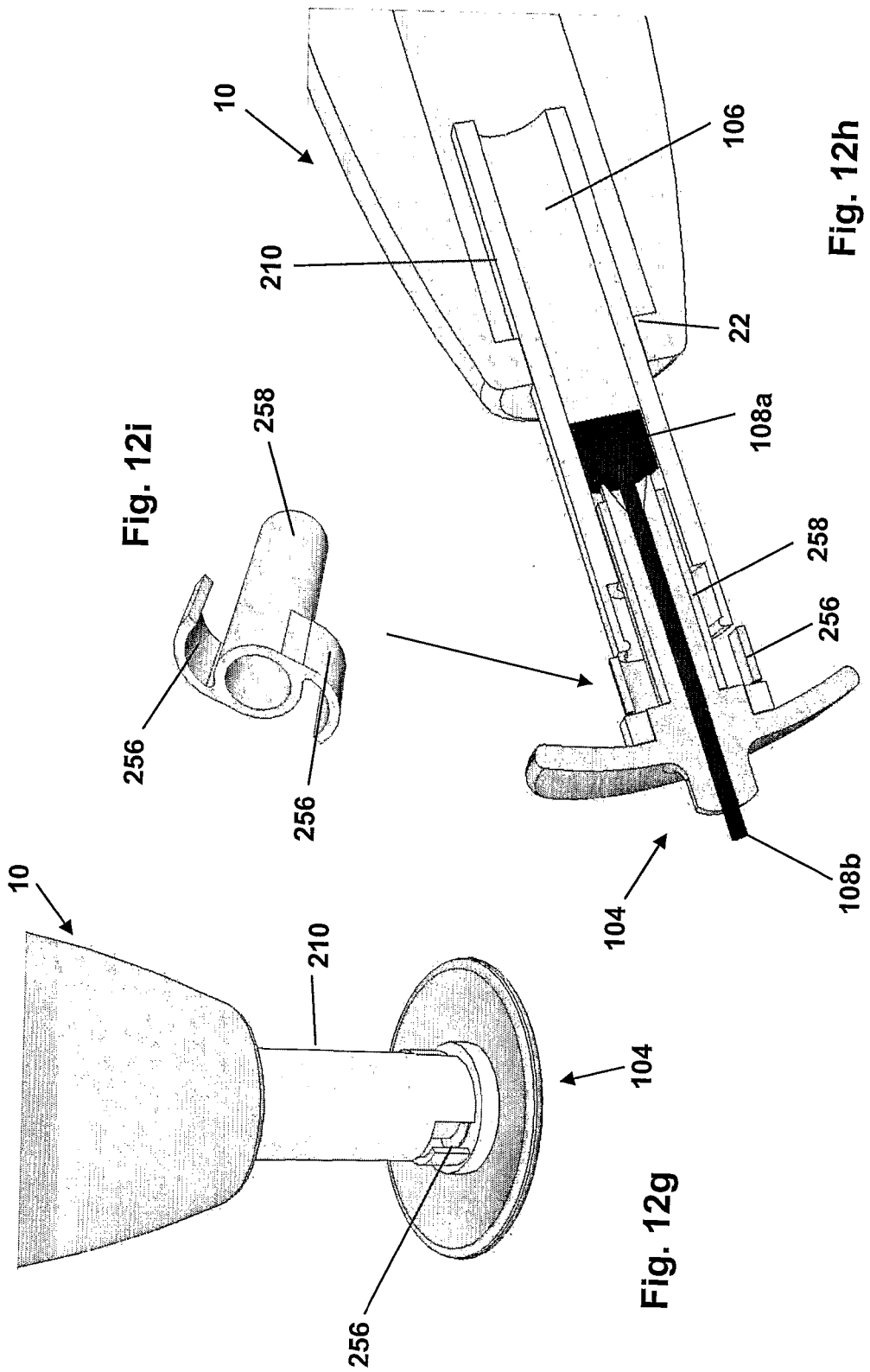

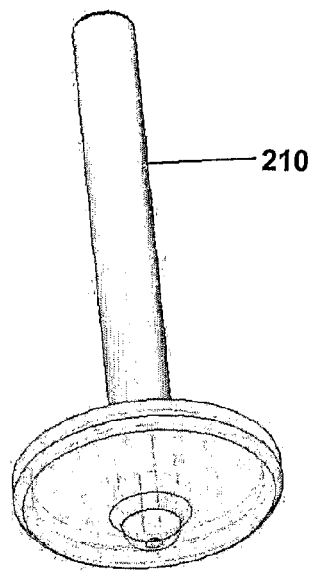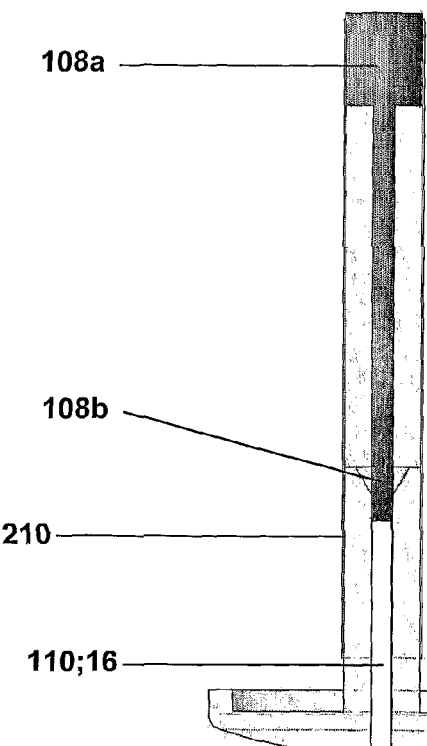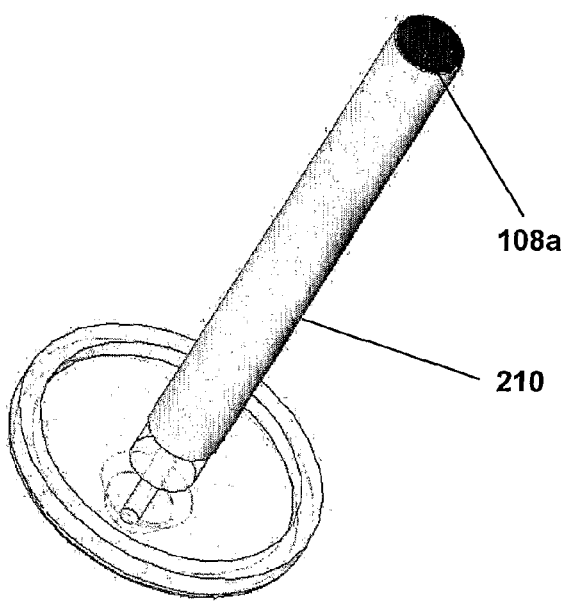
Fig. 13a
Fig. 13b
Fig. 13c

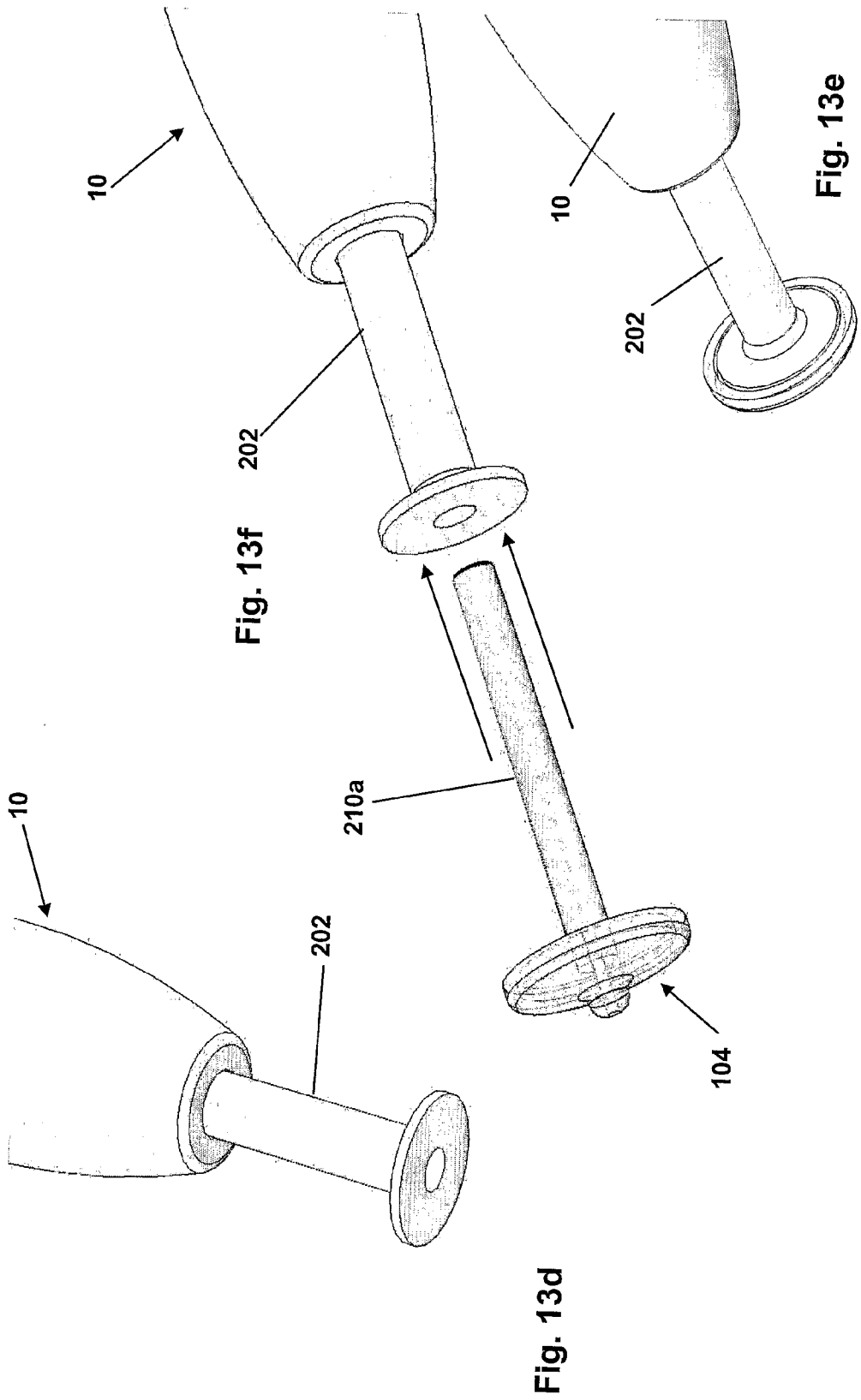

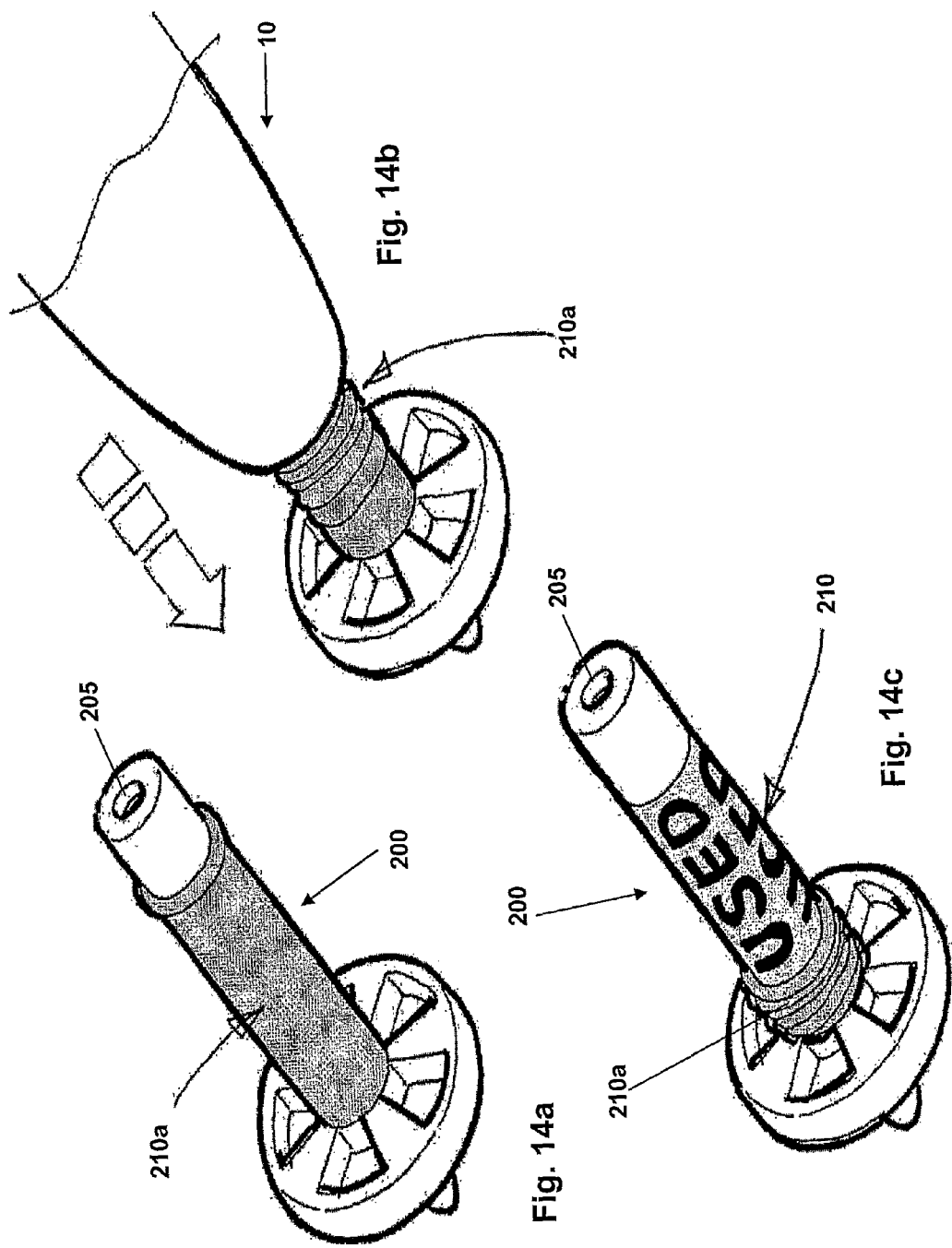

DISPOSABLE ASSEMBLY CONTAINING A SKIN PIERCING ELEMENT

CROSS-REFERENCES TO RELATED APPLICATIONS

This patent application claims priority to International Application No. PCT/GB2006/000411 having an international filing date of Feb. 7, 2006 which claims priority to GB 0502840.2 filed on Feb 7, 2005, all of which are incorporated herein by reference in their entirety.

FIELD OF THE INVENTION

The present invention relates to improvements in or relating to devices used in the fields of drug delivery or sampling. Such devices are used to deliver drugs (or other substances) or take samples by first piercing the skin, and may be used with humans or animals. In particular, the present invention relates to an assembly for use with an actuator device. More particularly, the present invention relates to a disposable assembly containing a skin piercing element, the actuator device which receives the assembly causing the skin piercing element to enter the skin, on actuation of the actuator device, to deliver a drug (or other substance) or take a sample. The present invention also relates to an assembly which displays an indication that it already has been used or is disabled and therefore made safe after actuation of the actuator device, such that the assembly is prevented from reuse and more preferably still the skin piercing element is safely housed in the assembly such that it does not constitute a "sharps" risk.

The term skin piercing element as used herein is used in a context which covers not only traditional capillary needles, but also other skin piercing or skin entering elements including, for example, lancets, drive pins, or a pioneer projectile.

BACKGROUND TO THE INVENTION

The applicant has developed a novel approach to drug delivery which is described in full in international patent applications PCT/EP02/10394 and PCT/EP03/07859. The content of both these applications are included by reference.

In international patent application PCT/EP02/10394 and referring in particular to FIG. 16 of PCT/EP02/10394, there is illustrated a delivery or actuator device fitted with a disposable assembly, the disposable assembly being referred to as a drug cassette. The disposable assembly comprises a casing having a central aperture or chamber in which is mounted an injectate comprising a pioneer projectile and a formulate or drug. The pioneer projectile may be inert or a pharmaceutical product. The pioneer projectile and drug may be separate or a single unit, for example, in the form of a single rod or pin or needle type structure; the pioneer projectile being the sharp or piercing end of the rod.

A large headed ejector pin (also referred to as a drive pin) comprising a flat head and an elongate body is positioned over the injectate so that when the ejector pin is contacted, in use, by a striker or hammer, the injectate is pushed along the central aperture or chamber and out into the patient. A resilient member, such as a rubber block, urges the ejector pin back a little after injection.

The disposable assembly is loaded into the actuating device by, for example, screwing it into the lowermost end of the inner housing.

The disposable assembly is shaped such that when it is in contact with the skin it pre-tensions the skin to actuation. This ensures that the injectate will penetrate the skin rather than just stretch the skin.

Where the ejector pin or drive pin is used with a needle or lancet the non skin contacting end of the needle or lancet may constitute the pin and typically, though not essentially, a drive head will be provided thereon.

The ejector pin is designed to push the injectate beyond the end of the actuator device by up to (say) 2.5 mm. This means that the end of the ejector pin (which preferably has the same profile and diameter as the end of the pioneer projectile) might just penetrate the skin to ensure that the injectate has been fully administered into the skin.

When the actuator device is actuated the striker or hammer travels along the striker guide until it contacts the head of the ejector pin with a force that causes the injectate to pierce the skin. The ejector pin continues to push the formulation into the patient to the required depth, which is determined by the length of the injectate and the extent to which it is pushed by the ejector pin. A rubber stop is squashed by the ejector pin head during delivery of the injectate but the elastic properties of the rubber stop enable the tip of the ejector pin to be withdrawn into the disposable component of the device.

The later filed application, PCT/EP03/07859, describes in more detail a drug delivery device suitable for delivering drugs using a pioneer projectile instead of a traditional needle to pierce the skin. However, the device may also be used to cause a traditional capillary needle or needle lancet to pierce the skin, as described with reference to FIG. 4 therein.

SUMMARY OF THE INVENTION

The present invention addresses a number of problems associated with the disposable assembly or drug cassette used in association with an actuator device of the type disclosed in international patent applications PCT/EP02/10394 and PCT/EP03/07859, but additionally has application in or with other devices used in either drug delivery to humans or animals or in the obtaining of samples from humans or animals.

In particular the principles and arrangements described can be used with skin piercing elements such as:
  Needle lancet assemblies;
  Capillary needle assemblies;
  'Tine' test assemblies; and
  Pioneer projectiles.

Thus, it is an object of the present invention to provide a disposable assembly containing a skin piercing element for an injection or sampling device which precludes re-use of the assembly once it has been actuated.

In this regard the ImplaJect® system described in international patent applications PCT/EP02/10394 and PCT/EP03/07859 is so easy to use, it is possible to reinsert a 'used' cassette or assembly into the actuator device and re-actuate the actuator device and assembly against the skin. This is an issue because:
  It may be believed that an injection has been made;
  There is a chance that the drive pin in the cassette, which protrudes from the cassette during the injection, strikes the skin of the patient; and
  If the cassette has previously been used on an infected patient then it is possible that an infection could be passed to another patient.

Such a drug cassette is designed to contain a drive pin, therapeutic agent or drug and a pioneer projectile as described in the patent applications identified. However, an alternative use of the cassette is to incorporate a capillary needle or lancet rather than a pioneer projectile. The capillary needle or lancet may be driven by a separate drive pin although it will be appreciated that in such circumstances a drive pin may not be necessary.

Needle lancets are commonly used by diabetics who need to take a sample of blood to check their blood glucose levels. Needle lancets are also used for obtaining samples for other medical conditions. For some diagnostic tests a sample of interstitial fluid, rather than blood, may be sufficient in which case a more superficial penetration of the skin is required. The depth of insertion of the lancet could be altered either by adjusting the spring strength within the ImplaJect® device or alternatively, assemblies could be produced with different length lancets.

It may also be possible to take tissue samples (biopsy) in addition to fluid samples.

Thus, for use with a needle lancet, the strength of the main 'driving' spring within the ImplaJect® device can be reduced from the force currently required for a pharmaceutical product. This is because a needle lancet can be a much finer diameter than a pharmaceutical product and have a much sharper tip. The rest of the design for the actuation device can otherwise be identical to the current ImplaJect® device.

Current designs for needle lancets either comprise a fully disposable device or they comprise a reusable actuator device and a disposable lancet. There are a number of issues with the current designs of needle lancet. These are:

- Some lancets do not 'auto-destruct' and can therefore be used more than once;
- Some lancets leave an exposed lancet following the procedure. It is possible that this lancet could be contaminated with a blood borne disease and it is therefore dangerous and care needs to be taken with disposal;
- Many of the lancet designs rely on the user pressing firmly on the target tissue and then actuating the device in order to obtain a successful skin prick. This process relies on the coordination of the patient to actuate the device when sufficient pressure is being applied to the tissue;
- Some of the reusable actuators for the needle lancets require multiple steps to load a lancet, actuate the device and then dispose of the lancet and so are inherently complicated;
- Some of the disposable lancets are more complicated and therefore more expensive to manufacture;
- Some of the lancets have removable 'tags' which must be removed by the patient prior to the needle prick. This means that there is subsequently more than one component to dispose of following the procedure.

Use of the ImplaJect® actuator device with a disposable assembly of the invention overcomes all of these issues which is not the case with current commercial designs of needle lancet.

An additional application of the needle lancet design would be to incorporate multiple lancets which could then be used for a 'Tine' test. This test has been used routinely in the past for testing for tuberculosis. A small quantity of tuberculin solution is coated onto a number of needle lancets which are pushed into the skin. The injection site is then assessed visually to determine if a reaction has occurred in the skin. This type of test could use single or multiple lancets in the assembly and could be adapted for any kind of allergy testing.

Thus, an ideal assembly design will not be able to be operatively inserted into the ImplaJect® device or an alternative actuator device such that it could be actuated for a second time. In this regard, it should be noted that a key feature of the ImplaJect® actuator device is it can only be actuated with a full depression stroke and can only be actuated again following completion of an actuation cycle.

According to a first aspect of the present invention there is provided an assembly for use with an actuator device comprising, i a housing configured to allow operative connection to the actuator device;

the housing having a channel adapted to receive a skin piercing element such that on actuation of the actuator device the skin piercing element is, at least in part, displaced from an end of the housing to penetrate the skin; and ii an indicating and/or disabling mechanism; the indicating mechanism signalling when the assembly has been used and the disabling mechanism rendering the assembly disabled, after actuation of the actuator device.

Preferably, the assembly is for single use only and can be disposed of after actuation of the actuation device and assembly.

The assembly may be fabricated from a number of components or as a single unit, for example, the assembly may be moulded or pressed as a single piece.

The force imparted by the actuator device to the assembly is sufficient to drive the skin piercing element to pierce the patient's skin. The force may be generated within the actuator device using a spring, for example. Preferably, the spring is a compression spring.

Generally speaking, actuation of the actuator device occurs when the assembly, connected to the actuator device, is pressed against the skin of a patient and sufficient force is applied to displace the skin piercing element from the end of the housing to penetrate the patient's skin. A single actuating cycle is completed when the force is released, removing the assembly from the patient's skin and the assembly and actuator device revert back to their original position relative to each other.

Preferably, the channel of the assembly contains a skin piercing element or plurality of skin piercing elements. The skin piercing element can be, for example, a needle, a plurality of needles, a capillary needle, a lancet, a solid needle, or a tine needle. The skin piercing element may also equally be a pioneer projectile.

The pioneer projectile may be inert or a pharmaceutical product. The pioneer projectile and drug may be separate or a single unit, for example, in the form of a single rod or pin or needle type structure; the pioneer projectile being the sharp or piercing end of the rod.

Preferably, the assembly comprises a stem for engaging the actuator device, the stem defining at least a portion of the channel. As pressure is applied to the actuator device by the user, this pressure builds as a force in the spring. When the force in the spring reaches a predetermined value, the actuator device is triggered and a hammer or striker travels along the stem imparting an impact force to the skin piercing element. Preferably, the stem is of a length to allow force generated by the actuator device to be delivered to the assembly. The length of the stem may also be varied to accommodate different lengths of skin piercing element.

Preferably, the assembly is manufactured from a minimal number of components to simplify manufacture. In a preferred embodiment the housing comprises two main components, a stem and a skin contacting component located at a leading end of the stem remote from the actuator device; the channel running the length of the stem and through the skin contacting component.

The skin contacting component has a primary skin tensioning surface. During actuation of the actuator device, the primary skin tensioning surface creates tension in the patient's skin at and around the point of entry of the skin piercing element. This local tensioning of the skin stimulates nerve ends at and around the area of contact between the primary skin tensioning surface and the patients skin making the patient's skin less sensitive to the skin piercing element, thus reducing the patient's discomfort caused by the skin piercing element.

Furthermore, the tensioning of the skin local to the point of entry of the skin piercing element not only reduces the skin thickness at the point of entry of the skin piercing element but also stretches the skin to create a stretched membrane having a substantially reduced elasticity compared to the un-tensioned skin, making it easier for the skin piercing element to penetrate the skin. This is particularly advantageous when using a pioneer projectile which may not be as able to penetrate skin as would a conventional needle, for example. Furthermore, skin tensioning local to the point of entry of the skin piercing element allows the use of a reduced force by the actuator device than would otherwise be required, again reducing the discomfort which would otherwise be caused to the patient.

The primary skin tensioning surface has a skin contact area greater than the skin contact area of the skin piercing element. The primary skin tensioning surface may be knob, spherical or part spherical in shape. Preferably, the primary skin tensioning surface is cone shaped, tapering towards a leading end. Preferably, the leading end of the cone is of a curved shape. Alternatively, the leading end of the cone maybe be truncated giving it a flattened end. The diameter of the leading end of the primary skin tensioning surface is less than 6 mm. Preferably, the diameter of the primary skin tensioning surface is less than 3 mm.

The skin contacting component may also have a secondary skin tensioning surface located intermediate the primary skin tensioning surface and a trailing end of the assembly. The skin contact area of the secondary skin tensioning surface is greater than that of the primary skin tensioning surface. The secondary skin tensioning surface spreads the tension force applied to the skin by the primary skin tensioning surface over a larger area thus further reducing the discomfort of the patient.

Preferably, the skin contact surface of the secondary skin tensioning surface is curved. For example, the secondary skin tensioning surface maybe spherical or mushroom shaped.

Preferably, the diameter of the secondary skin tensioning surface is at least equal to the diameter of the actuator device.

Preferably, the secondary skin tensioning surface is curved at an angle of between 0° to 45° relative to a longitudinal axis of the actuator device and in the direction from leading end to trailing end of the assembly.

The skin contact surface of the primary and/or secondary skin tensioning surface maybe roughened to improve the tensioning of the skin contacting the skin tensioning component.

The disposable assembly may advantageously include a drive pin located within the housing, the drive pin communicating force generated by the actuator device to the skin piercing element. This allows the force to be more effectively channeled from the actuator device to the skin piercing element.

Preferably, the drive pin has a diameter equal to, or substantially equal to, the diameter of the skin piercing element. Optionally, the drive pin has a greater diameter than the skin piercing element. The drive pin may also have a more substantial or thickened end portion adjacent the actuator device, further improving the channeling of force between the actuator device and the skin piercing element.

Preferably, the thickened end portion of the pin lies flush with the inner wall surface of the stem promoting smooth movement of the pin along the channel.

The disabling mechanism is a design feature of the assembly. The actuator device and assembly can't be re-actuated until the disposable assembly has been withdrawn from the actuator device after the actuation cycle is completed. In general, the disabling mechanism may operate in two ways;
 i. cause the configuration of the stem of the assembly, by which it is operatively connected to the actuator device, to be altered in a manner which restricts movement of the actuator device along the length of the stem which is required to complete actuation of the assembly; or
 ii. cause the needle or other skin piercing or skin entering element to be automatically locked within the channel in a position such that it is precluded from being reused even when actuation of the actuator device is attempted.

The disabling mechanism of the assembly includes at least one actuatable member. Actuation of the actuator device causes the operation of the actuatable member. The actuatable member moves from a first position before actuation of the actuator device to a second position after actuation of the actuator device. Movement of the actuatable member from the first to the second position prevents a subsequent use or actuation of the assembly by the actuator device.

Typically, the disposable assembly is T shaped when viewed in transverse section, the T's cross piece forming the skin contacting component and the stem serving as the male mating member for insertion into the female mating member (opening) of the actuator device. In this configuration the assembly is slidably mounted in the actuator device. Thus, if all or a part of the stems configuration is altered by the action of the actuatable member or members, after actuation of the assembly by the actuator device, then the assembly can not be reactuated because the actuator device is restricted from moving down the length of the stem required to actuate the assembly.

The actuatable member or members may, for example, extend in a lateral direction across the channel after actuation of the actuator device restricting a second actuation of the assembly by the actuator device.

The actuatable member or members may extend outwardly of the stem wall to restrict the actuator device sliding along the length of the stem. For example, the stem of the assembly's housing, which serves as the male member for insertion into the female member (opening) of the actuator device, is modified such that on use, a single actuating member is, after actuation of the actuator device, able to extend through an aperture (or apertures) in the stem wall so as to prevent re-actuation of the assembly by the actuator device by restricting sliding of the actuator device along the stem of the assembly.

More specifically, the assembly may comprise an actuating member such as a sprung or hinged ring which is seated in the channel in a first position. In this first position it is in a compressed or folded state due to the restraining effect of the channel forming walls of the stem. However, when the actuator device is actuated the skin piercing element and/or drive pin is pushed along the channel and into a patient. At the same time, the actuating member is moved down the channel until on completion of actuation of the actuator device, the actuating member is aligned with the aperture(s) in the stem and partially expands into the aperture(s) such that is unable to move back up the channel as the skin piercing element and/or drive pin is retracted after actuation of the actuator device into the channel by the action of a return spring. On completion of actuation of the actuator device, the ring is unable to fully expand because the outer surface of the stem wall is in abutment with the inner wall of the actuator device, i.e. the actuator device is fully depressed along the stem. However, after actuation of the actuator device, the actuator device slides back along the stem away from the skin contacting component and back to its original position such that the sprung or hinged ring is able to fully expand such that it extends beyond the aperture(s) preventing the actuator device sliding along the length of the stem and thus preventing the actuation of the assembly for a second time. The effect is that the assembly becomes disabled after first actuation.

It is also envisaged that part of the stem wall itself may be displaced in an axial direction after actuation of the assembly by the actuator device, restricting movement of the actuator device along the length of the stem and thus disabling the assembly after first actuation.

More specifically, the housing may comprise a first actuatable member (e.g. a release plunger), which when acted upon during the actuating action of the device is moved from a first position in which it acts as a locking member, by acting as a stop to a second actuatable element, (e.g. a slide detent or a portion of the stem wall), to a second position in which it leaves the second actuatable member free to move from a first position, in which it lies flush with the rest of the stem wall to a second radially expanded position under the action of a resilient member (e.g. a compression wing spring which may be integral with the second actuatable element) which is prevented from exerting it's force until after actuation of the actuator device. This is because the actuator device, once fully depressed along the stem will hold the moveable portion of the stem wall in position. After actuation, the actuator device slides back along the stem returning to its original position and allowing the spring to radially expand the portion of the stem wall. This action will restrict movement of the actuator device along the length of the stem preventing further actuation of the assembly by the actuator device, thus disabling the assembly.

The disabling mechanism may be an integral part of the assembly housing and in the embodiment referred to above comprises a first actuatable member and a second actuatable member having associated therewith a resilient member.

Alternatively, the actuatable member or members may extend inwardly of the stem wall to restrict movement of the needle or drive pin. The actuatable members may, for example, trap the thickened end portion of the drive pin, preventing or restricting its further movement along the channel of the assembly after first actuation of the assembly, thus disabling the assembly. The actuatable member(s) may lock the needle or drive pin in an extended position or allow the needle or drive pin to be withdrawn back into the housing by the action of a return spring, for example, and lock the needle or drive pin in the retracted position thus preventing the actuator device driving the needle or drive pin from the housing on further actuation of the assembly by the actuator device, thus disabling the assembly.

One way of achieving this is by the provision of a pair of actuatable members, e.g. sprung stem wall members, which are biased to move into the channel but which are precluded from doing so by opposing slidable counter biasing members present in the channel which act against the actuatable members until they are moved away therefrom, during actuation of the actuation device More specifically, a first sprung stem wall member is, at rest, precluded from moving to it's favoured position by a first counter biasing member, e.g. the head of the drive pin, and a second sprung stem wall member is, at rest, precluded from moving to it's favoured position by a second counter biasing member, e.g. a ring member.

However, on actuation of the actuator device, the needle and drive pin are pushed down the channel taking the ring member with it. As the needle and drive pin travel down the channel the drive pin head which, prior to actuation of the actuator device, counters the first sprung stem wall member, reaches a point where it no longer restrains the sprung stem wall member and so the sprung stem wall member is able to move into the channel above the drive pin's head thereby preventing retraction of the needle/drive pin. As the drive pin continues to travel down the channel the head of the pin makes contact with the second counter biasing member and together the two continue to move down the channel. At this point the drive pin's head replaces the ring member as the second counter biasing member and the ring member is moved further down the channel.

It is only after actuation the actuator device, when the needle and drive pin retract up the channel by the action of a light coil spring or other resilient member and once the drive pin's head returns past the second sprung stem wall member that the second sprung stem wall member is able to move into the channel thus retaining the needle/drive pin such that it is trapped between the two actuated sprung stem wall members.

This design of assembly will still enable the assembly to be placed in, for example, the ImplaJect® device. However, actuation of the actuator device will not enable the pin (or lancet) to be pushed from the assembly.

Alternatively, the actuatable member or members may be located on a shaft of the needle or drive pin, which after actuation of the assembly by the actuator device, extend outwardly from the needle or drive pin to engage a stop member within the stem which prevents the needle or drive pin being withdrawn back into the assembly. In this way, it is visually clear to a user that the assembly has already been used and will appropriately dispose of the used assembly and replace it with an unused assembly. In this way, the disabling mechanism may also act as an indicating mechanism.

Preferably, the indicating mechanism is a deformable member located on the exterior of the stem along a length thereof, the deformable member engagable with the actuation device on actuation thereof.

The deformable member may be, for example, a cover for the stem. The cover being of a frangible material surrounding at least a portion of the length of the stem. On actuation of the actuator device, the actuator device slides along the stem, engages the cover and crumples the cover between the actuator device and the skin tensioning component. The crumpled cover is a visual indication that the assembly has been used which will prompt the user to dispose of the used assembly in an appropriate manner and to replace the used assembly with a new un-used assembly. In addition, the external surface of the stem beneath the cover may have a sign further visually indicating that the assembly has been used when the cover is crushed to reveal the sign. The sign may be, for example, a suitable word such as "used". The sign may be luminescent for ease of visual recognition.

Alternatively, the cover may have a weakened section which is crushed on actuation of the assembly by the actuator device. The weakened section may be a prefolded or corrugated section of the cover.

It will be appreciated that the features of these alternative approaches and embodiments can be combined.

According to a further aspect of the invention there is provided an actuator device fitted with an assembly of the invention. Whilst such an assembly will generally be used with a reusable device, it could form part of a single use disposable actuator device.

Various aspects and embodiments of the invention will now be described, by way of example only, with reference to FIGS. 1 to 16. FIGS. 1 to 3 are included by way of background and describe a known actuator device, it's mode of operation and an assembly of the prior art, referred to as a cassette, containing a pioneer projectile and pin assembly. The actuator device and assembly of FIGS. 1 to 3 are more fully described in international patent applications, PCT/EP02/10394 and PCT/EP03/07859.

BRIEF DESCRIPTION OF THE DRAWINGS

FIG. 4b is a plan view of the assembly of FIG. 4a;

FIG. 5a is a cross sectional view taken along a longitudinal axis of another embodiment of disposable assembly according to the present invention (shown in part and in a state prior to actuation) comprising an alternative disabling mechanism;

FIG. 5b is a similar view of the assembly of FIG. 5a shown during actuation of the actuator device;

FIG. 5c is a similar view of the assembly of FIG. 5a shown after actuation of the actuator device and in a disabled state;

FIG. 6a is a cross sectional view taken along a longitudinal axis of a further embodiment of disposable assembly according to the present invention (shown in part and in a state prior to actuation of the actuator device) comprising an alternative disabling mechanism;

FIG. 6b is a similar view of the assembly of FIG. 6a shown during actuation of the actuator device;

FIG. 6c is a similar view of the assembly of FIG. 6a shown after actuation of the actuator device and in a disabled state;

FIG. 7a is a side view of an assembly of the present invention shown attached to an actuator device, the assembly clearly showing a skin contacting component at a leading end thereof comprising a primary skin tensioning surface in the form of a truncated cone and a mushroom shaped secondary skin tensioning surface;

FIG. 7b is a cross sectional side view of the assembly and actuator device of FIG. 7a taken along a longitudinal axis thereof, showing internal components of the assembly and actuator device;

FIG. 9c is a perspective view of the assembly of FIG. 9b in which the drive pin, locked in position, is clearly visible at the leading end of the assembly;

FIG. 9d is an exploded perspective view of the assembly of FIG. 9a;

FIG. 10g is an exploded perspective view of the assembly of FIG. 10a;

FIG. 11b is an end view from the trailing end of the assembly of FIG. 11a;

FIG. 11c is an exploded perspective view of the assembly of FIG. 11a;

FIG. 11d is perspective view from a different angle of the assembly of FIG. 11a, shown here connected to an actuator device (shown in part);

FIG. 11e is a cross sectional side view of the assembly and actuator device of FIG. 11d taken along a longitudinal axis thereof, the actuator device shown here closer to the skin contacting component of the assembly;

FIG. 12a is a partially transparent side view, showing internal components, of another embodiment of disposable assembly illustrating an alternative combined disabling and indicating mechanism, the assembly shown connected to the actuator device (shown in part) and prior to actuation;

FIG. 12b is a side view of the assembly and actuator device of FIG. 12a;

FIG. 12c is a side view of the assembly and actuator device of FIG. 12a after actuation of the actuator device, clearly showing the wings extending through apertures in the stem wall of the assembly, thus restricting movement of the actuator device along the length of the stem, thus disabling the assembly preventing further actuation;

FIG. 12g is a perspective view of the assembly and actuator device of FIG. 12c;

FIG. 12h is a further perspective view of the assembly and actuator device of FIG. 12g shown here in cross section taken along a longitudinal axis of the assembly and actuator device (shown in part);

FIG. 12i is a perspective view of the disabling or indicating winged component of the assembly of FIG. 12a;

FIG. 13a is a perspective view and from the leading end of another embodiment of disposable assembly illustrating an indicating mechanism in the form of a cylindrical cardboard covering or foil having a weakened or pre-folded portion which crumples on engagement with the drive pin during actuation of the actuator device, thus visually illustrating when the assembly has been used, the assembly shown here prior to actuation of the actuator device;

FIG. 13b is a perspective view and from the trailing end of the assembly of FIG. 13a;

FIG. 13c is a cross sectional side view taken along a longitudinal axis of the assembly of FIG. 13a, showing internal components;

FIG. 13d is a perspective view of an actuator device having a disposable elongate extended portion for receiving the assembly of FIG. 13a;

FIG. 13e is a perspective view, from a different angle, of an actuator device of FIG. 13d;

FIG. 13f is a perspective view demonstrating insertion of the assembly of FIG. 13a into the elongate extended receiving portion of the actuator of FIG. 13d, the arrows indicating the direction of travel of the assembly;

FIG. 13i is a perspective view of the assembly of FIG. 13a removed from the actuator device after completion of the actuation cycle, clearly showing the crumpled portion of the cardboard covering, thus giving a visual indication that the assembly has been used and should be disposed of;

FIG. 14a is a perspective view and from the trailing end of an embodiment of disposable assembly similar to FIG. 13a illustrating an indicating mechanism in the form of a cardboard covering which surrounds the stem and crumples completely on engagement with the actuator device during actuation, thus visually illustrating when the assembly has been used, the assembly shown here prior to actuation of the actuator device;

FIG. 14b is a perspective view of the assembly of FIG. 14a together with actuator device, shown in part, the actuator device travelling in the direction of the arrow on actuation of the actuator device engaging and crumpling the cardboard covering surrounding a length of the stem;

FIG. 14c is a perspective view of the assembly of FIG. 14a after actuation of the actuator device and its removal therefrom, showing the crumpled cardboard covering and fluorescent sign underneath, clearly indicating that the assembly has been used and should be disposed of;

DETAILED DESCRIPTION

Figure 1:
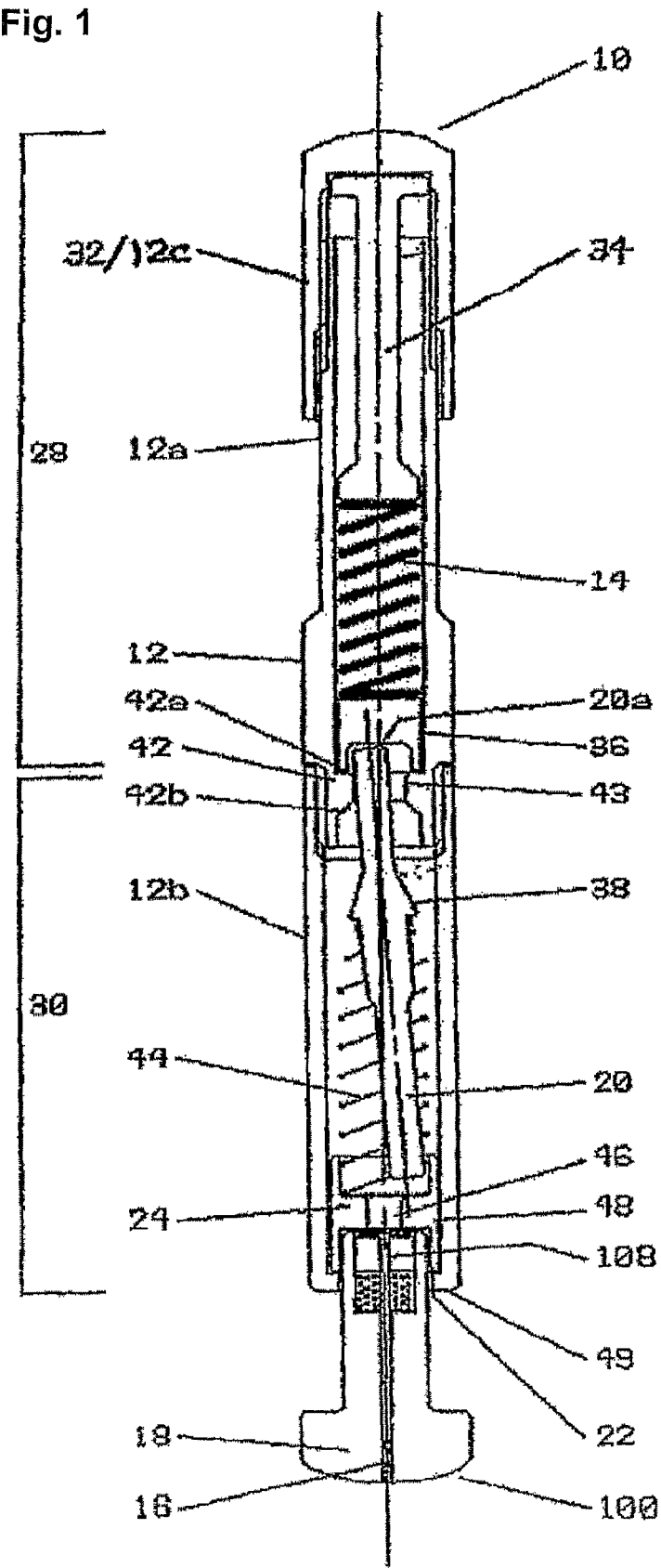
FIG. 1 is a cross-sectional view, taken along a longitudinal axis, of a reusable actuator device and assembly of the prior art.

FIG. 1 illustrates a reusable drug delivery or actuator device (10), with a packaged drug assembly (100) fitted thereto. The drug delivery device or actuator device (10) and packaged drug or assembly (100) are generally in the shape of a pencil and mushroom respectively. The drug delivery device (10) generally comprises the following components:

i) a housing (12);
ii) a compression spring (14) for generating a force capable of pushing a drug (16) from a packaging (18) into a human or animal body;
iii) an elongate bar or impact hammer (20) for transmitting said force to push the drug (16) from the packaging (18) into the human or animal body;
iv) an opening (22) in the delivery device (10) at a leading end thereof for receiving the packaged drug (100);
v) a means (24) for priming the actuator device; and
vi) a means (38,42b) for triggering the actuator device.

In the context of the present invention it is important to appreciate that:

1. The packaged drug (100) is an assembly (200) which may be disposed of after a single actuation cycle;
2. The drug delivery device or actuator device (10) can be reused for many actuations although there are certain applications where both the actuator device (10) and assembly (200) may be thrown away after a single actuation cycle;

3. The opening (22) and lower chamber (30) of the actuator device (10) allow the assembly (200) to be operatively connected to the actuator device (10).

In the embodiment shown in FIG. 1, the actuator device (10) is primed and triggered, i.e. actuated, in a single action.

The actuator device (10), which may be absent of the packaged drug (100), is spring powered. It can deliver the drug or a formulation containing a therapeutic compound (hereafter drug) in a solid, semi-solid or liquid form. By altering the form of the assembly (100), it may be used to either deliver drugs through a retractable needle, behind a pioneer projectile (FIG. 3), or it can also be used to deliver a solid drug splinter. Furthermore it can be used to operate a lancet.

Looking at the actuator device (10) in more detail it comprises a number of components which are readily assembled and easily sterilised making manufacture cheap.

The body of the actuator device (10) comprises a three part housing (12) including a first housing component (12a) defining a trailing barrel (28) which houses the compression spring (14), a second housing component (12b) defining a leading barrel (30) which houses the packaged drug or assembly (100) and the means (20) for transmitting the force to push the drug (16) from its packaging (18). The first and second housing components (12a; 12b) connect to one another, and a third housing component (12c), which preferably takes the form of a screw cap (32), fits over the end of the first housing component (12a) to close off the trailing barrel (28).

Within the upper barrel (28) is fitted the compression spring (14) for generating the force capable of pushing the drug (16) from its packaging (18). In the embodiment shown in FIG. 1, the compression spring (14) can generate a force of from about 10-40 N, more preferably 15-35 N and most preferably 18-31 N. Where the skin piercing element is a lancet it is likely that the required spring force from the actuator device (10) will be lower than the required spring force for a drug application because of the sharper point on a lancet, the smaller diameter of a lancet compared to a drug and a more superficial penetration of the skin with a lancet compared to a drug injection. The compression spring (14) is connected at a leading end to a spring follower (36) which is slidably mounted in the upper barrel (28). At a trailing end of the spring (14) is located a compression bar (34) which provides a contact surface against which the spring (14) can act. By screwing or unscrewing the cap (32) from the housing component (12a) the spring (14) can be caused to compress or relax thereby providing a means for adjusting the force that can be generated by the spring (14). In FIG. 1 the spring (14) is shown at minimum pre-load.

The trailing barrel (28) and leading barrel (30) are separated from one another by a wall (42) with a communicating aperture (43) therein and it is on the upper surface (42a) of the wall (42) that the spring follower (36) sits. The elongate bar (20) for transmitting the force generated by the spring (14) takes the form of an impact hammer (20) at a trailing end of the bar (20a), the trailing end (20a) of the impact hammer (20) passes through the communicating aperture (43) where it contacts the spring follower (36). In use the impact hammer (20) slides through the communicating aperture (43) pushing the spring follower (36) to the trailing end of the actuator device (10) causing the spring (14) to be compressed thus priming the actuator device (10).

Within the leading barrel (30) is housed not only the majority of the impact hammer (20), but a slewing spring (44) and a sliding piston (48) having an aperture (46) therein, such that the lower barrel can operatively communicate with the packaged drug or assembly (100) which is secured to the device via the opening (22) provided at the leading end (49) of the actuator device (10).

Prior to actuation of the actuator device (10), the slewing spring (44) functions to draw the longitudinal axis of the impact hammer 20 off centre. This is shown most clearly in FIG. 2a. However, the impact hammer (20) is adapted by way of a shaped shoulder region (38), (which in a preferred embodiment is substantially frustoconical, as illustrated) to be drawn into axial alignment with the aperture (46) in the sliding piston, against the action of the slewing spring (44), such that when it is fully primed the actuator device (10) automatically actuates. Accordingly, the lowermost surface (42b) of the wall (42) is shaped to receive the shaped shoulder region (38) of the impact hammer (20) and cause the impact hammer (20) to be axially aligned with the aperture (46) in the sliding piston (48) such that the impact hammer (20) is driven by the spring (14) through the aperture (46) in the sliding piston (48) where it contacts a drive pin (108) or other element causing the drug (16) or in alternative embodiments e.g. a lancet to be pushed out of its packaging (18) into the human or animal. In contrast with the FIG. 1 embodiment it should also be noted that the leading end (20a) of the impact hammer (20) graduates to a point (being substantially conical) and is seated in a similarly shaped recess (36a) in the spring follower (36). The shaping of the leading end (20a) of the hammer (20) and the provision of the similarly shaped recess (36a) in the spring follower (36) further improves reliability of actuation.

Figure 2A:
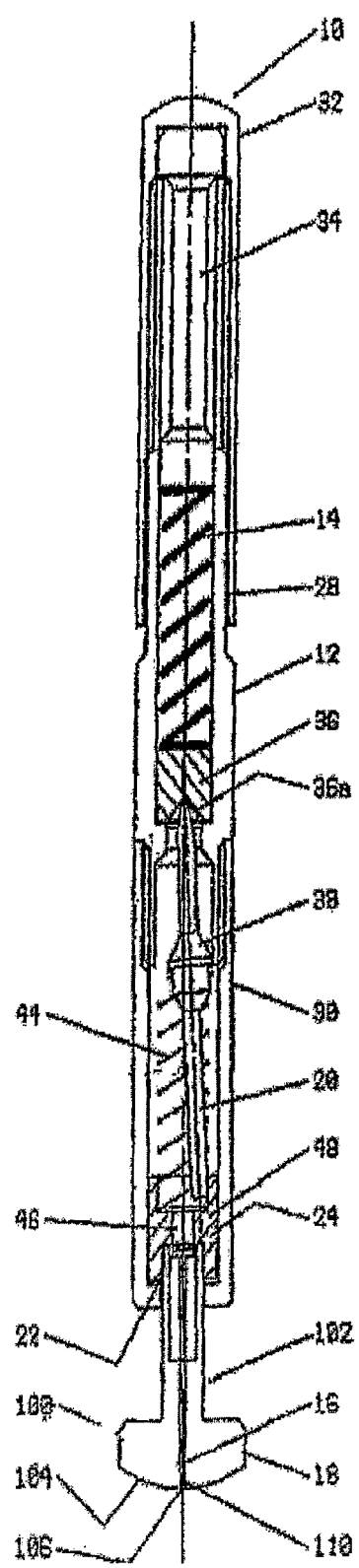
FIG. 2a illustrates the actuator device and assembly of FIG. 1 prior to actuation of the actuator device.
Figure 2B:
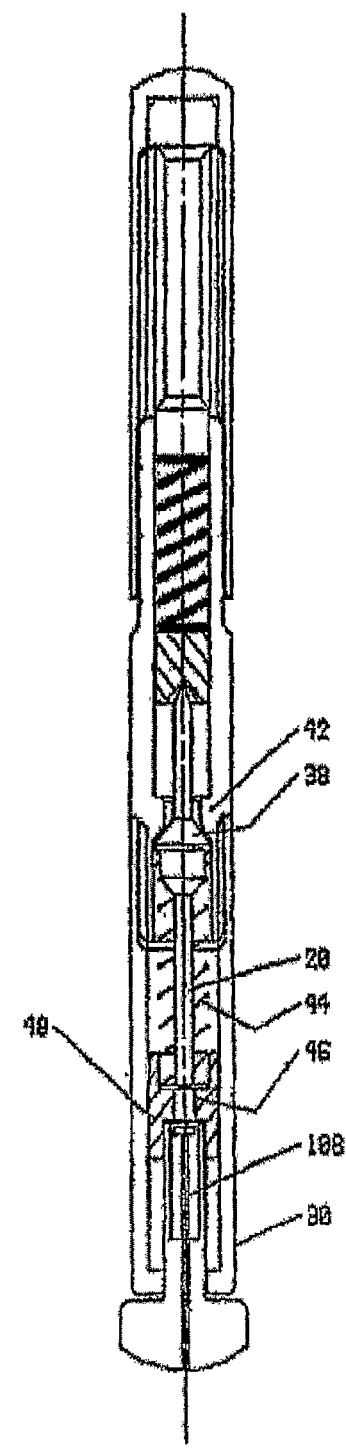
FIG. 2b illustrates the actuator device and assembly of FIG. 1, the actuator device fully depressed along a stem of the assembly during actuation of the actuator device.
Figure 2C:
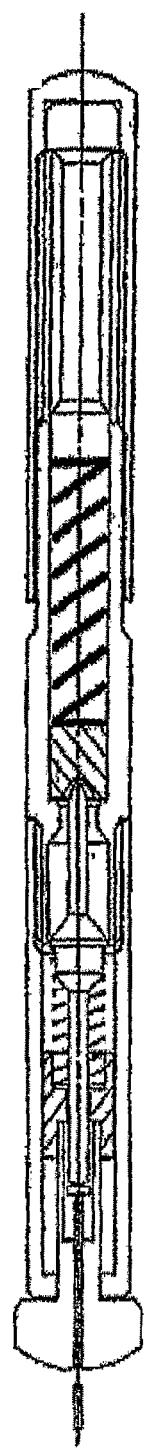
FIG. 2c illustrates the actuator device and assembly of FIG. 1 after actuation of the actuator device clearly showing a skin piercing element (in this case, a pioneer projectile) being ejected from the assembly.

By comparison of FIG. 2a with FIGS. 2b and 2c it will be apparent that once a packaged drug or other disposable assembly (100) has been attached to the leading end (49) of the actuator device (10), the assembly (100) and actuator device (10) can be actuated by a user holding the actuator device (10) about the housing (12) and pressing the assembly (100) firmly against the patients skin. This causes the packaged drug or other disposable assembly (100) to slide up the lower chamber (30) pushing the piston (48) which in turn pushes the impact hammer (20). As it does so the upper end (20a) of the impact hammer pushes against the spring follower (36) causing the spring (14) to be compressed until the necessary drive force is reached. This is at the point illustrated in FIG. 2b. At this point the shaped shoulder region (38) is drawn into the shaped lowermost surface (42b) of wall (42), the action of the slewing spring (44) is countered, the spring (14) is fully charged or compressed and the impact hammer (20) axially aligned with the aperture (46) in the sliding piston (48) such that it will automatically actuate, the spring (14) forcing the impact hammer (20) through the aperture (46) in the piston (48) causing it to push the drive pin (108) which in turn, depending on the mechanism employed in the assembly (100) (see FIG. 3) causes the drug to be dispensed or a needle or lancet to pierce the skin. Significantly the longitudinal axis of the impact hammer can't be aligned with the aperture (46) in the sliding piston (48) until a set actuating force is reached which is set to coincide with the point at which the shaped shoulder region (38) contacts the shaped lowermost surface (42b) of wall (42) thus providing a safety mechanism against accidental actuation. When the set actuating force is reached, triggering is automatic and the actuator device (10) is actuated (FIG. 2c).

It should be noted that on actuation of the actuator device (10) and assembly (10), the hammer (20) moves a short distance, less than 10 mm, more preferably less than 5 mm and typically about 3 mm before impacting the drive pin (108) and therefore moves (say) approx 5 mm before the pioneer projectile (110) strikes the skin. This means that the maximum force and impact are all in the first few millimetres of travel, when the maximum force is required to pierce the skin. Through the rest of the delivery, the force is reducing as the main spring (14) power is diminishing and also the slewing spring (44) is being compressed (FIG. 2c). This means that the force tapers off during the second half of the delivery when less force is required.

Therefore the force profile through the whole delivery matches the requirements, i.e. a high force and impact to pierce the skin and then a reduced force to push the injectate into the skin.

In the case of a reusable actuator device (10) the packaged drug or other disposable assembly (100) is removed from the actuator device 10 and discarded. The slewing spring (44) will assist in this action. As the packaged drug or other disposable assembly (100) is removed from the device the slewing spring (44) acts to draw the impact hammer (20) so that it is not axially aligned with the aperture (46) in the piston (48) and the device (10) is ready to receive a new packaged drug or other disposable assembly (100).

It is not possible to actuate the actuator device 10 for a second time until the drug package or other disposable assembly (100) has been partially withdrawn from the device and the slewing spring (44) has drawn the impact hammer (20) so that it is not axially aligned with the aperture (46) in the piston (48).

Such an actuator device (10) and assembly (100) can be used to dispense a drug in a variety of different forms depending on how it is packaged. Samples may also be taken and the device (10) may thus be used to operate an assembly (100) having a needle lancet, for example. In this case the generating force may be reduced by using a weaker spring (14).

Figure 3:
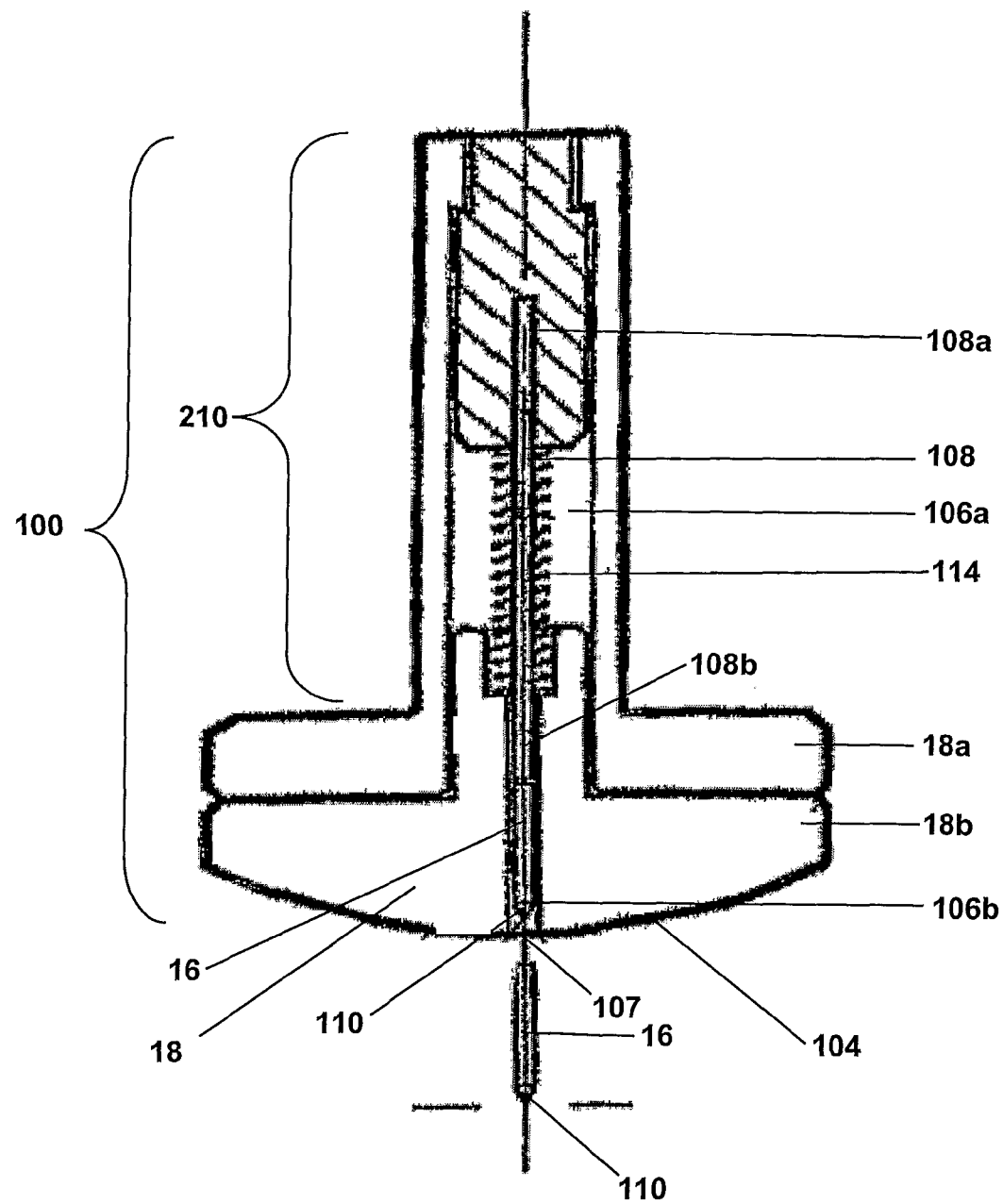
FIG. 3 is a more detailed view of the assembly (packaged drug) of FIGS. 1 and 2 shown here with the pioneer projectile/drug in a first position prior to actuation of the actuator device, housed within the assembly, and a second position, ejected from the assembly after actuation of the actuator device.

Referring now to FIG. 3, the assembly (100) containing a drug takes the form of an end piece which is adapted to be slidably mountable in the actuator device (10). The packaging (18) takes the form of a two-piece housing (18a, 18b), thereby simplifying construction and assembly. A first housing element (18a) is in the shape of a hollow inverted "T" and comprises a region (210) (the stem of the "T") which serves in use to slidably engage the device (10) allowing the assembly (100) to slide up the leading chamber (30) of the actuator device (10), and a "cross piece" against which the second element (18b) abuts. A central channel (106) runs through the middle of the stem exiting at the crosspiece. The second element (18b) comprises an end (104) which is shaped to tension the skin. The second element (18b) is also substantially the shape of an inverted T and has a channel (106b) running down the centre axis of the inverted T. The respective channels (106a, 106b) communicate with one another to form a single channel (106) which runs right through the assembly (100). The channel (106b) houses a pioneer projectile (110) and the drug (16) or a drug splinter (effectively 110,16), the skin contacting end of which is set a few millimetres in from the skin tensioning surface of the device to ensure it is moving at the requisite speed when it contacts the skin. It also houses the leading end (108b) of the drive pin (108). At the end remote from the skin tensioning surface (104) the channel (106b) opens out to house a resilient member e.g. a spring (114). The placing of a resilient member under the head (108a) of the drive pin (108) allows the drive pin (108) to be withdrawn back into the housing immediately after actuation. The drive pin (108) is slidably mounted in the channel (106) so that when the head (108a) is depressed by the hammer (20) of the actuator device (10) the drive pin (108) moves down the channel (106) pushing the pioneer projectile (110) and drug (16) from the channel (106b) through an opening 107 into the human or animal body. The pioneer projectile (110) and drug (16) are held in place in the channel (106b) by, for example, a breakable membrane (not shown) or appropriate frictional means e.g. one or more markings or splines on either the pioneer projectile (110), drug (16) and or channel (106b) surface.

Having described the actuator device (10) and one embodiment of a prior art cassette (100) (disposable assembly) we turn to a detailed description of the disposable assemblies of the present invention.

Figure 4A:
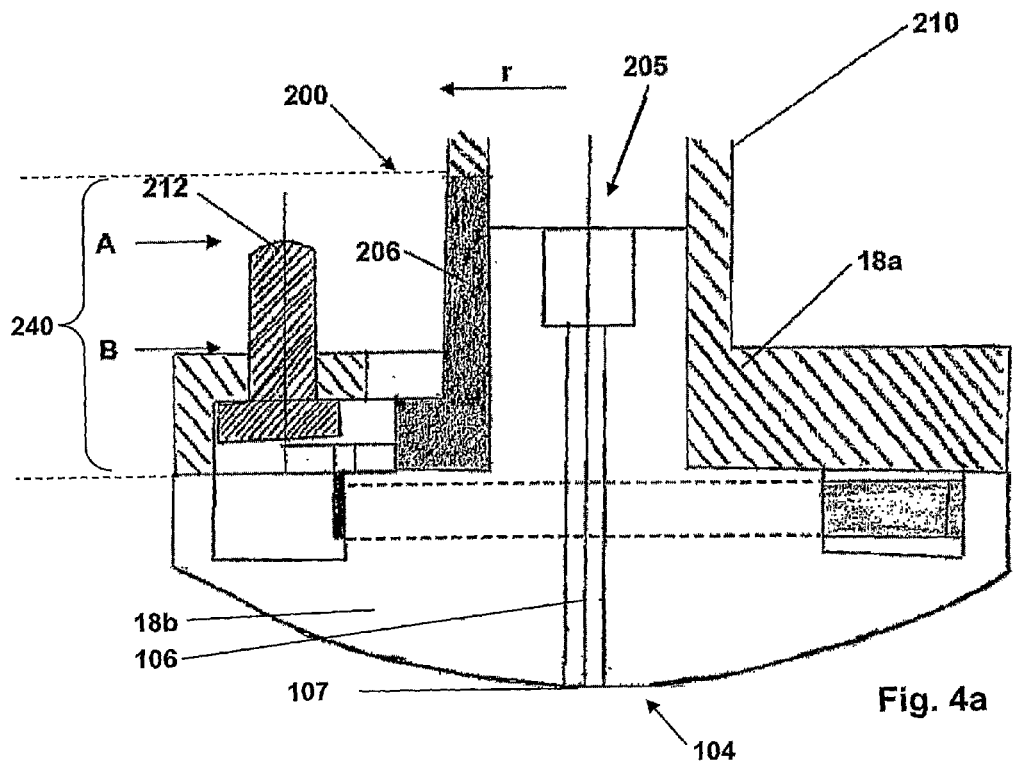
FIG. 4a is a cross sectional view taken along a longitudinal axis of a disposable assembly comprising a disabling mechanism according to the present invention, shown here without skin piercing element or drive pin.
Figure 4B:
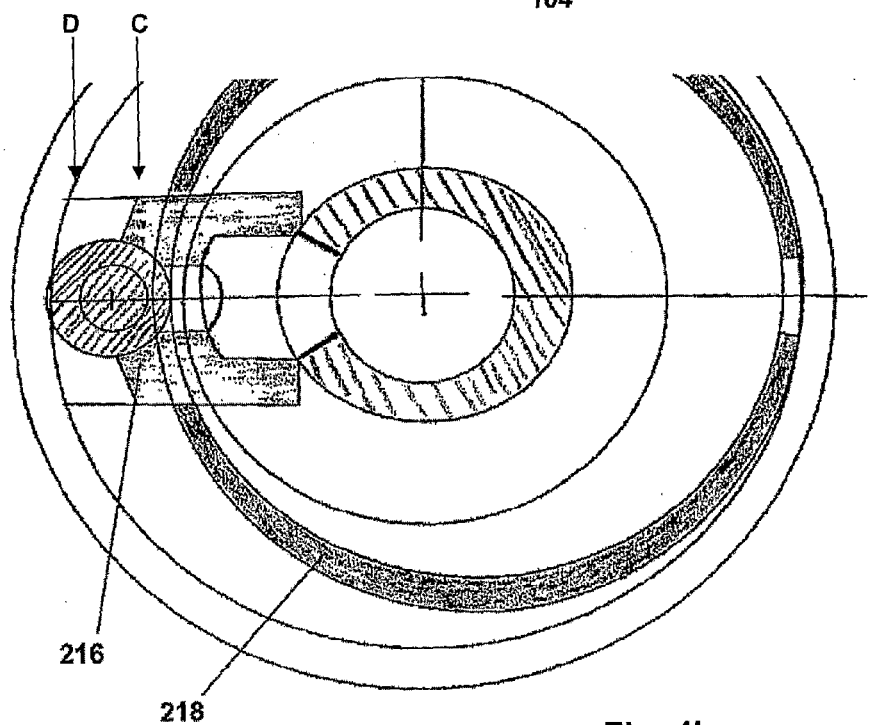

Referring initially to FIGS. 4a and 4b it will be noted that the disposable assembly (200) of the present invention comprises;

i a housing (250) configured to allow operative connection to the actuator device (10); the housing having a channel (106) adapted to receive a skin piercing element (110; 16) such that on actuation of the actuator device the skin piercing element is, at least in part, displaced from an end (107) of the housing to penetrate the skin;

and ii an indicating and/or disabling mechanism (240); the indicating mechanism signalling when the assembly has been used and the disabling mechanism rendering the assembly disabled, after actuation of the actuator device.

The assembly (200) is generally mushroom shaped having an elongate cylindrical stem portion 210 which defines a section of the channel 106 and the head of the mushroom shaped assembly defining a skin contacting component 104. The channel (106) defines a through passageway, running from a trailing end 106a of the stem 210 where it engages with the actuator device 10, through the skin contacting component 104. The passageway terminates at both ends of the channel with a stem opening 205 at a trailing end of the stem 210 for receiving the impact hammer (20) into the channel (106) and with an opening 107 at the end (106b) of the housing through which the skin piercing element 110 is pushed by the action of the actuator device 10.

The disabling mechanism (240) forms part of the housing (250) and comprises a first actuatable member (212), more specifically a release plunger, which when acted upon during the actuation of the actuation device 10, is moved from a first position (A) (in which it acts as a locking member by acting as a stop to a second actuatable element (216), more specifically a slide detent) to a second position (B) in which it leaves the second actuatable member (216) free to move from a first position (C) to a second position (D) under the action of a resilient member (218), more specifically a compression wing spring, which is prevented from exerting it's force until the disposable assembly (200) is at least partially withdrawn from the device (10).

Preferably, the housing 250 is manufactured from a minimal number of components to simplify assembly. In a preferred embodiment only two main components are required, and indeed it would be possible to have a single piece, hinged about the channel axis. The two components are a first, stem forming, housing element (18a) and a second, skin contacting, housing element (18b). The additional components forming the disabling mechanism (240) may be an integral part of the housing (250) and in the embodiment referred to above comprise a first actuatable member (212) and a second actuatable member (216) having associated therewith a resilient member (218).

Importantly, part of the housing 'alters shape' after actuation of the actuator device 10 such that the assembly 200 cannot be actuated again as the assembly 200 will no longer operatively connect to the device 10.

Because the assembly has been designed for use with the ImplaJect™ actuator device (10) the disposable assembly (200) is shaped as an inverted "T" when viewed in transverse section, the cross piece (18b) forming the skin contact surface (104) and the outer surface (204) of the stem (210) serving as the male mating member for insertion into the female mating member (opening) of the device (10). Referring back to FIGS. 1 and 2 this is the opening (22) of the lower chamber (30) of the actuator device 10.

In use the assembly 200 is fitted to the ImplaJect® actuator device 10 by sliding the stem (210) into the opening (22) of the device (10). Actuation of the actuator device 10 causes the first actuation member (212) to be depressed from position A to position B. Then, after actuation of the actuator device 10, the second actuation member (216) is able to move from position C to D under the influence of resilient member (218) causing a section (206) of the stem (210) to expand radially (r) such that the assembly 200 can not be operatively refitted into the device (10) on further occasions.

FIGS. 5a-5c illustrate a second embodiment of this first approach. In this embodiment the assembly (200) is illustrated in part cross section only. It also comprises a substantially T shaped housing (250) comprising a cross piece (18b) providing a skin contacting surface (104) and a stem (210) for inserting the assembly (200) into an actuating device. An outer surface (204) of the main stem (210) serves as the male mating member for insertion into the female mating member (opening 22) of the device (10).

In this embodiment the main stem (210) of the assembly's housing includes a through aperture (209) or apertures at or near it's juncture with the cross piece (18b).

The channel (106) houses a needle (220) or other skin piercing or skin entering element which in use is temporarily pushed out of the opening (107) at the end (106b) of the assembly (200). It is pushed by the action of, for example, the hammer 200 of the ImplaJect® actuator device (10) acting on the head (108a) of a drive pin (108) or some similar element such as the needle (220).

An actuating member (216), which in the example takes the form of a sprung or hinged ring, is seated in the channel (106) in a first position "E". In this position it is held in a compressed or folded state due to the restraining effect of the channel forming innermost walls of the stem (210). However, when the device is actuated a force acts upon the head (108a) of drive pin (108) and pushes the drive pin and needle (108/220) down the channel (106) beyond opening (107) and into a patient. At the same time, the actuating member (216) is slidably moved down the channel until at the delivery point, position "F" (FIG. 5b), it is aligned with the aperture (209) in the stem (210) and partially expands into the aperture such that it is unable to move back up the channel (106) as the needle (220) is retracted by the action of a return spring (226). In this position it is unable to fully expand because the outer surface (204) of the stem wall (210) is in abutment with the inner wall of the device (10). However, after actuation of the assembly by the actuator device 10 the actuating member (216) is able to fully expand, such that it extends beyond the aperture (209) preventing the disposable assembly from being refitted into a device to an extent necessary for further use.

In a third embodiment there is provided an assembly (200) and a disabling mechanism (240) which causes the needle, after use, to be automatically locked in a position such that it is precluded from leaving either end of the channel (106), but in particular it is prevented from leaving the end (106b; 107) of the channel on subsequent attempts to actuate the actuator device (10).

One way of achieving this is illustrated in FIGS. 6a-6c. In this embodiment the stem wall (210) of the assembly is provided with a pair of actuatable members (212b; 216b). These actuatable members are biased to move into the channel (106) but are prevented from doing so until the device is actuated by opposing channel bridging members (232, 234) which act against the actuatable members until they are moved therefrom during the act of actuation. In fact, the head (108a) of drive pin (108) acts as the first channel bridging member (232) and a plastic ring member acts as the second (234) channel bridge member. The spacing (S) between the actuatable members and the relative size (S1) of the first channel bridging member is significant as will be apparent from the explanation given below:

Thus, in a first position, (FIG. 6a) the channel bridging members (232, 234) act against the actuatable members (212b; 216b). However, when the assembly is acted upon by actuation of device (10), and the impact of hammer (20) contacts the head (108a) of drive pin (108), the drive pin and needle (108/220) are pushed down the channel (106) such that the uppermost channel bridging member (232) no longer resists the natural bias of the first actuatable members (212b) and thus it moves inwardly into the channel to act as a stop preventing reuse.

Similarly, the pin head (108a) draws bridging member (234) down the channel (106) but as the head (108a) does so it acts against the second actuatable member (216b) preventing it from moving inwardly into the channel during mid injection. However, as the drive pin and needle (108/220) are retracted by the action of return spring (226) (FIG. 6c), pin head (108a) moves back up the channel such that it no longer counters the second actuatable member (216b) which moves inwardly of the channel. The drive pin (108) which may be attached to a traditional needle is thus retained between the two actuated members (212b; 216b).

Further embodiments of the assembly of the present invention will now be described with reference to FIGS. 7 to 16. Similar features of the invention will be designated with the same reference numerals.

Figure 8:
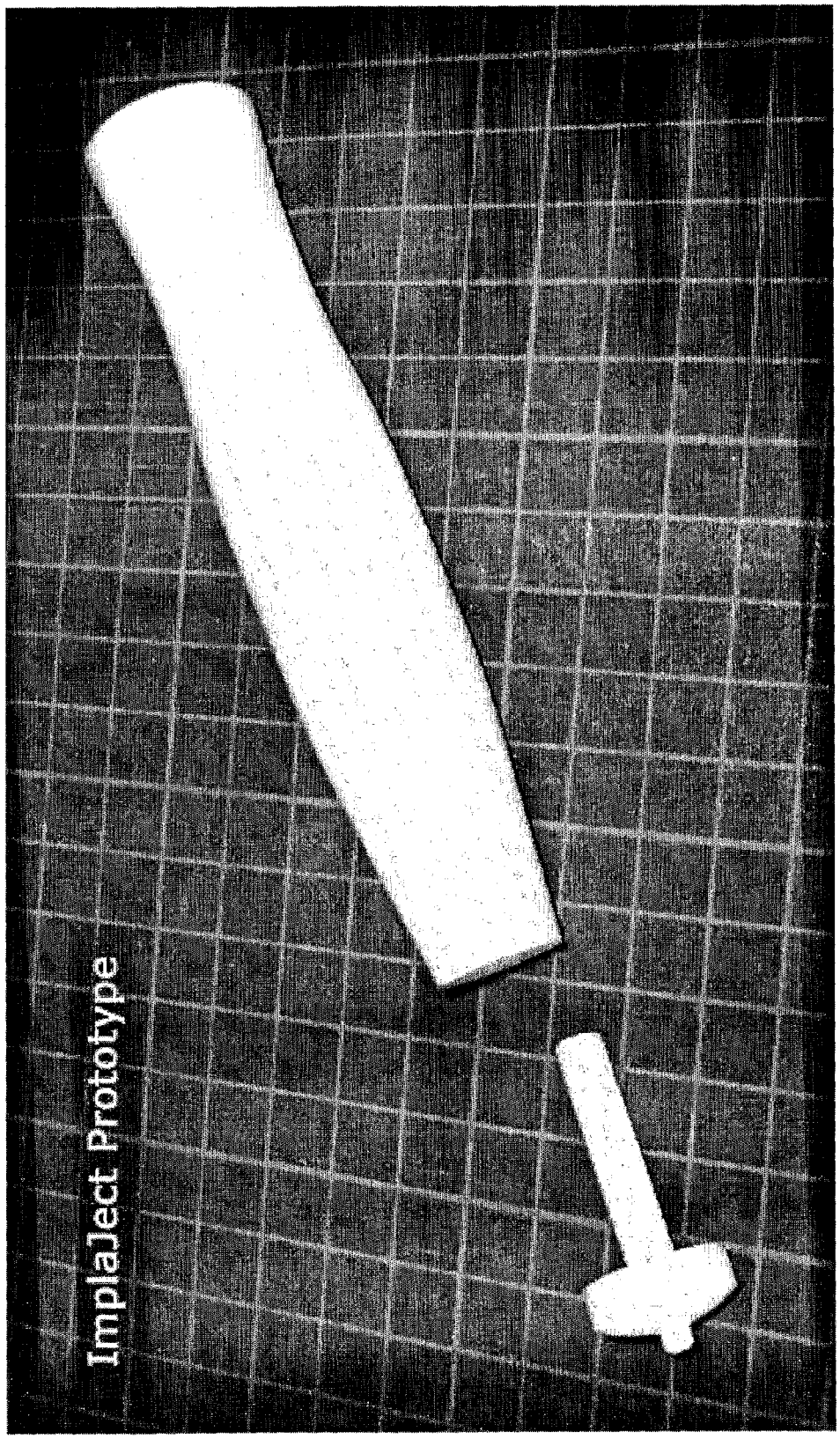
FIG. 8 is a perspective view and from above of the assembly of the present invention and an actuator device, shown here in a disconnected state.
Figure 9A:
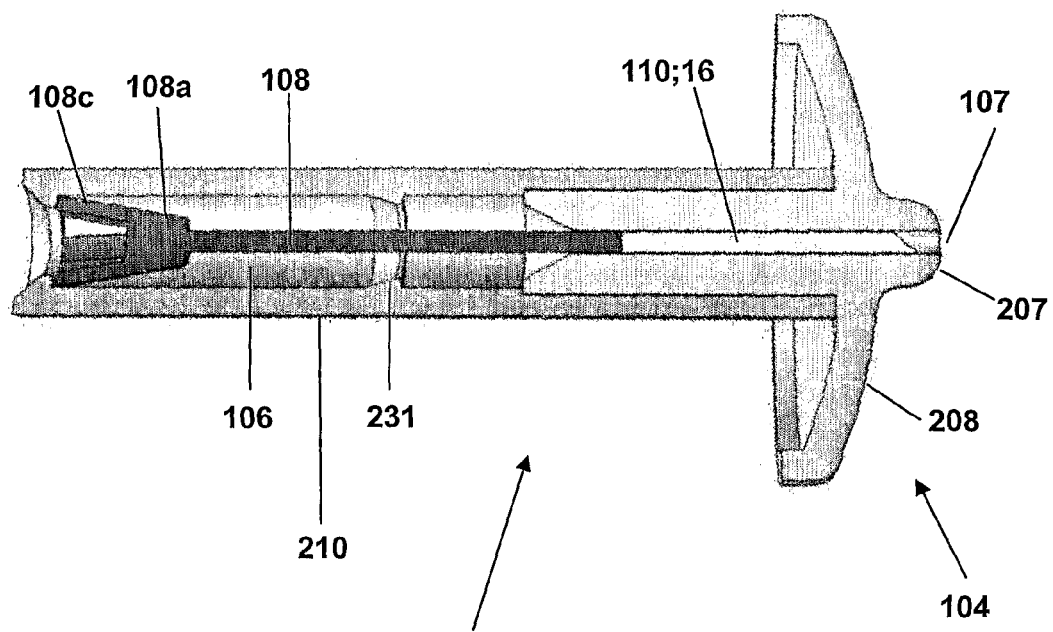
FIG. 9a is cross sectional view taken along a longitudinal axis of another embodiment of disposable assembly showing a combined disabling and indicating mechanism, the assembly illustrated prior to actuation of the actuator device.
Figure 9B:
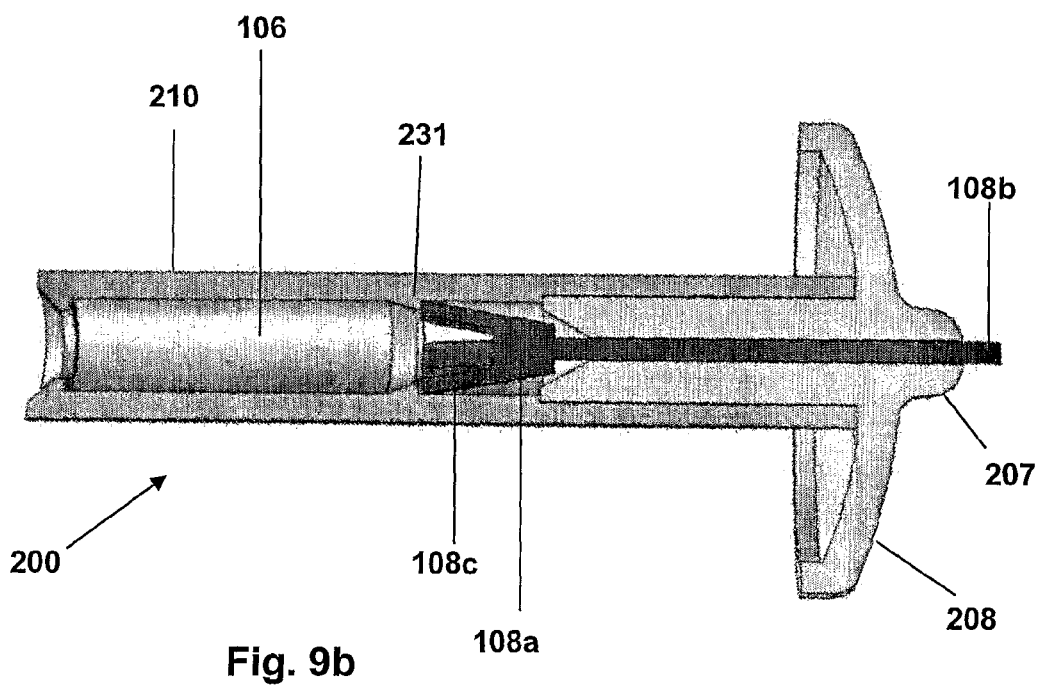
FIG. 9b is similar view to the assembly of FIG. 9a, showing the assembly after actuation of the actuator device.

Referring initially to FIGS. 7a, 7b and 8, there is shown an actuator device 10 and assembly 200 of the present invention. In this embodiment, the assembly 200 includes a pioneer projectile as the skin piercing element 110. The assembly 200, in particular shows the skin contacting component 104 having a primary skin tensioning surface 207 located at the leading end of the assembly 200 such that it is the first area of the assembly 200 to contact the surface of the patient's skin and a secondary skin tensioning surface 208, located adjacent the primary skin tensioning surface 207. The primary skin tensioning surface 207 is a truncated cone shape, tapering towards the leading end of the assembly 200. The secondary skin tensioning surface 208 continues from the cone, flaring outwardly and towards a trailing end of the assembly into the shape of the head of a mushroom.

During use and actuation of the actuation device 10, the cone 207 is pressed against the patient's skin creating tension in the patient's skin at and around the point of entry of the pioneer projectile. This tensioning, local to the point of entry of the pioneer projectile into the skin, stimulates nerve ends at and around the area of contact between the cone 207 and the patients skin making the patient's skin less sensitive to the pioneer projectile, thus reducing the patient's discomfort caused by piercing of the skin by the pioneer projectile 110.

The tensioning of the skin local to the point of entry of the pioneer projectile 110 also reduces the skin thickness at the point of entry of the pioneer projectile making it easier for the pioneer projectile 110 to penetrate the skin. As such, the skin tensioning local to the point of entry of the pioneer projectile 110, created by the action of pressing the cone shaped surface 207 against the patient's skin, allows the use of a reduced force by the actuator device 10 than would otherwise be required, further reducing the discomfort which would be caused to the patient by using a conventional syringe with needle.

To create the proper tension in the patient's skin the truncated face of the cone 207 should be of an area greater than the skin contact area of the pioneer projectile. In this embodiment, the diameter of the truncated cone 207 is 3 mm. The curved surface of the cone 207 progressively flares outwardly from the truncated end thus gradually increasing the contact area with the patient's skin. This helps stimulate nerve ends over a greater area of the patient's skin.

The mushroom shaped secondary skin tensioning surface 208 has a larger skin contact area than that of the cone shaped primary skin tensioning surface 207. The mushroom surface 208 spreads the tension created in the skin by the cone 207 over a larger area of the skin thus even further reducing the discomfort of the patient.

The skin contact surface area of the cone 207 and mushroom 208 is dimpled to provide a roughened contact surface area to improve the tensioning of the skin by the skin contacting component 104.

Referring now to FIGS. 9a to 9d, there is illustrated another embodiment of disposable assembly 200 showing a combined disabling and indicating mechanism 240.

There is located along a midportion of the channel 106 a tapered section 231 which tapers towards the leading end of the assembly 200 thus narrowing the channel 106 along the tapered section, after which the channel 106 reverts back to its original diameter. The drive pin 108 has actuable members in the form of flexible fins or wings 108c located on the trailing end 108a of the shaft of the drive pin 108 and flaring towards the trailing end of the assembly 200. During actuation of the actuator device 10 and assembly 200, the drive pin 108 is pushed by the hammer 20 along the channel 106 and through the tapered section 231. On travelling through the tapered section 231, the flexible wings 108c are compressed inwardly by the tapered walls of the channel 106 so that the drive pin 108 may travel beyond the tapered section 231. Once the drive pin 108 is clear of the tapered section 231, the flexible wings 108c expand outwardly to contact the inner wall of the channel 106. At this stage, the assembly 200 has been fully actuated by the actuator device 10, the pioneer projectile has penetrated and entered the patient's skin and the leading end 108b of the drive pin 108 protrudes from the opening 107 at the end (106b) of the housing 250. After actuation of the assembly 200 and actuator device 10, the drive pin 108 is prevented from retracting back into the channel 106 as the wings 108c engage the tapered section 231 which acts as a stop member. In this way, the assembly 200 can not be reloaded with another drug and needle or pioneer projectile, thus disabling the assembly 200. Furthermore, the protrusion of the drive pin 108 from the opening 107 makes it visually clear to a user that the assembly 200 has already been used and will appropriately dispose of the used assembly 200 and replace it with an unused assembly 200. In this way, the disabling mechanism may also act as an indicating mechanism.

FIGS. 10a to 10i illustrate an alternative disabling and indicating mechanism 240.

Figure 10A:
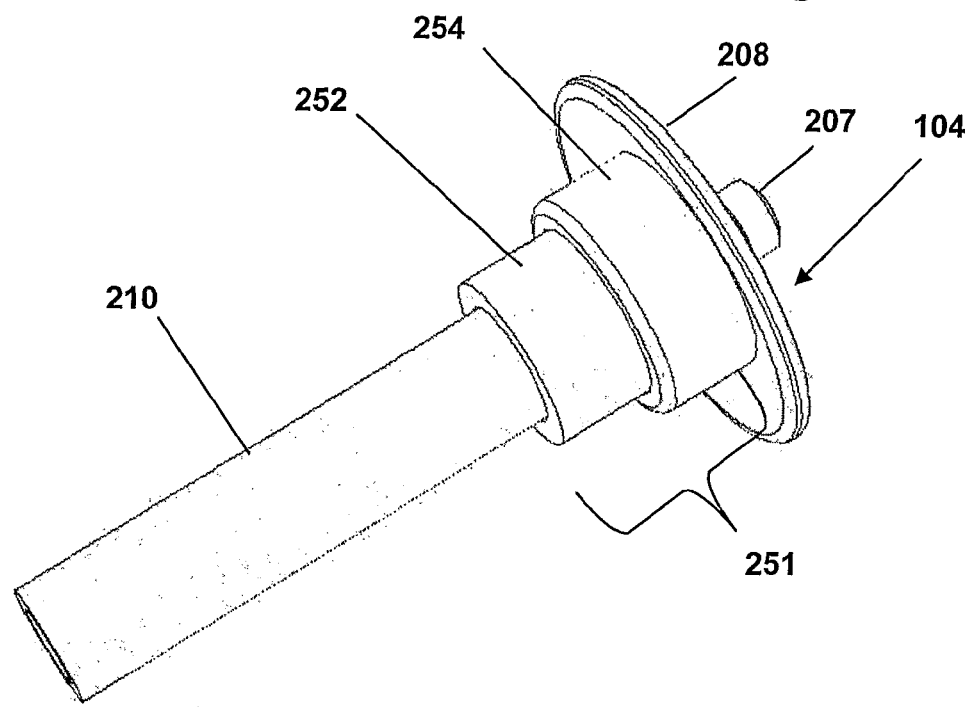
FIG. 10a is a perspective view of yet another embodiment of disposable assembly showing an alternative combined disabling and indicating mechanism, the assembly illustrated prior to actuation of the actuator device.
Figure 10B:
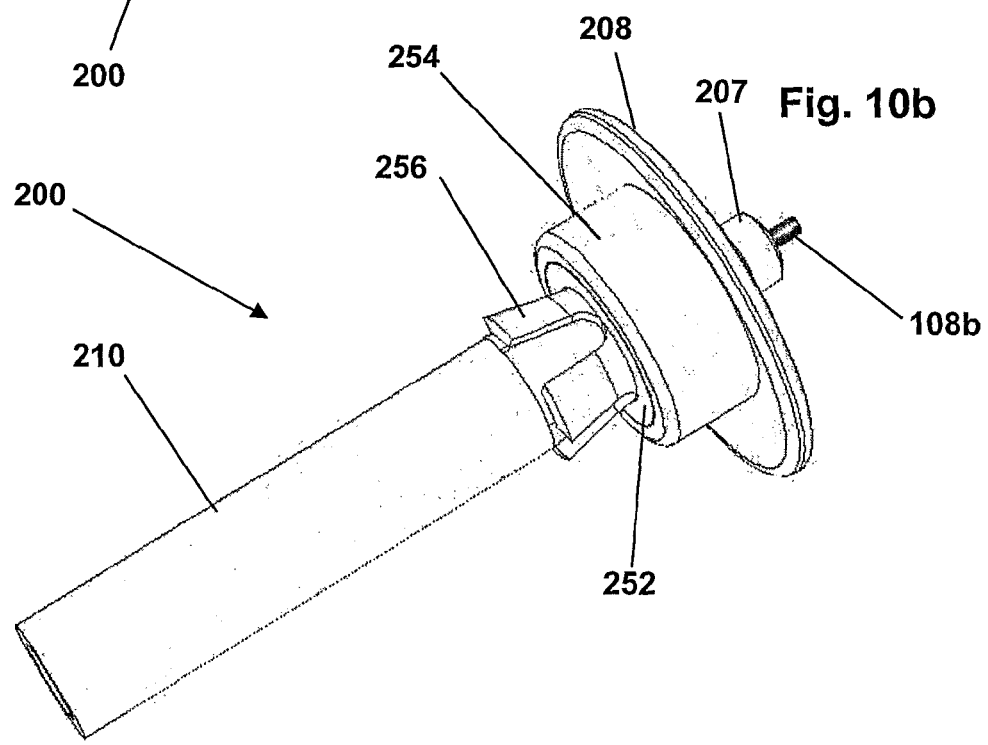
FIG. 10b is similar view to the assembly of FIG. 10a showing the assembly after actuation, expandable wings intermediate the skin contacting component and stem clearly visible and restricting movement of the actuator along the stem inhibiting further actuation.
Figure 10C:
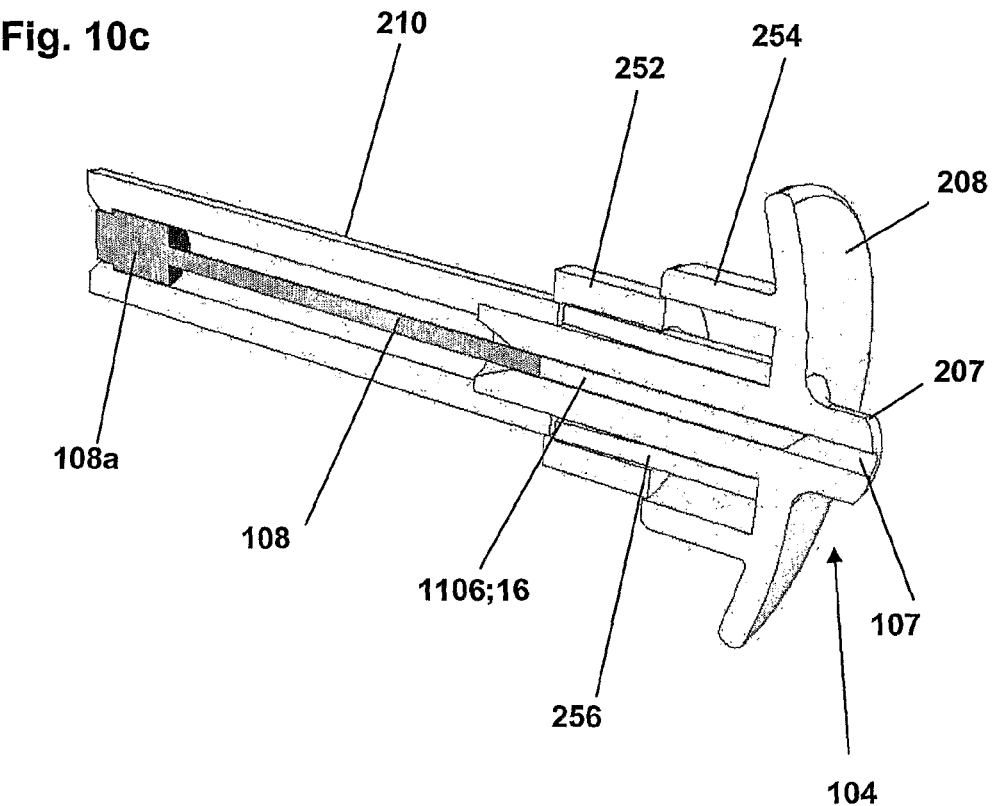
FIG. 10c is a cross sectional perspective view of the assembly of 10a taken along a longitudinal axis thereof and showing internal components of the assembly.
Figure 10D:
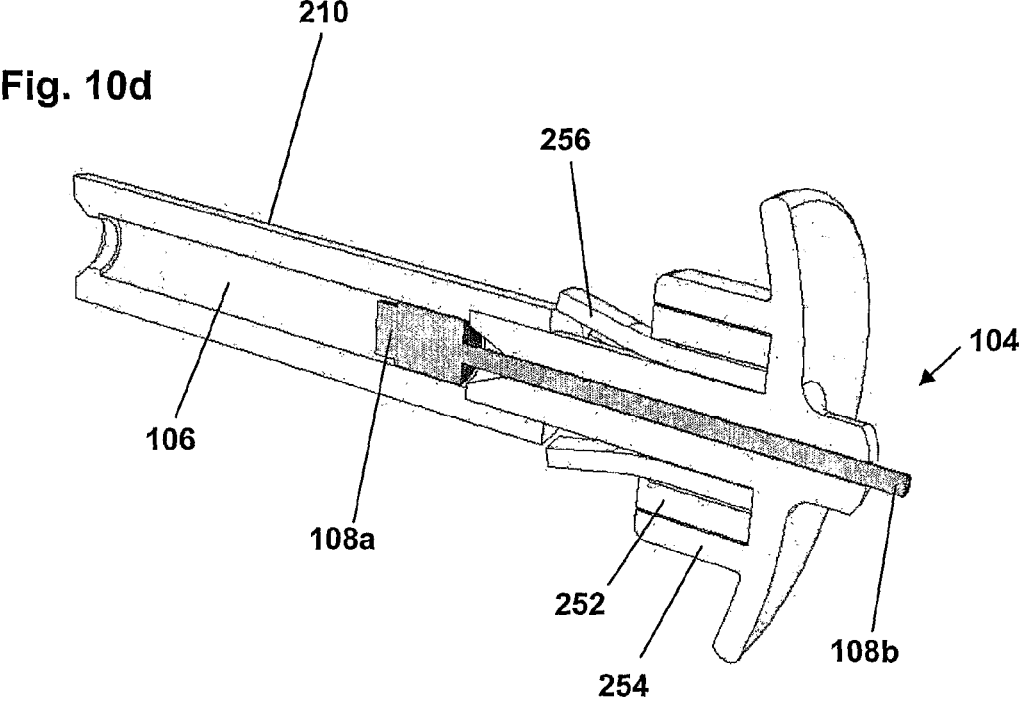
FIG. 10d is a cross sectional perspective view of the assembly of 10b taken along a longitudinal axis thereof and showing internal components of the assembly.
Figure 10E:
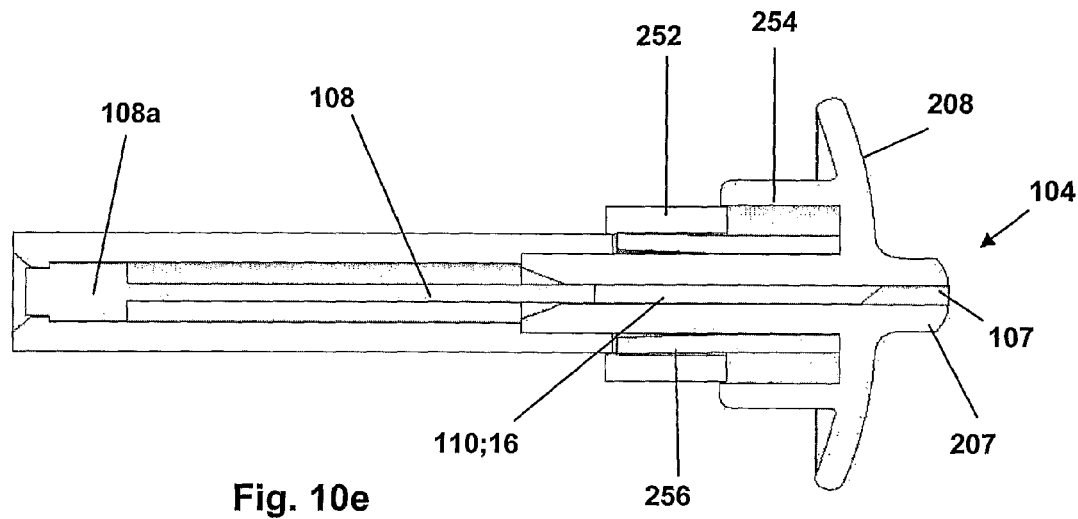
FIG. 10e is a cross sectional side view of the assembly of 10a taken along a longitudinal axis thereof and showing internal components of the assembly.
Figure 10F:
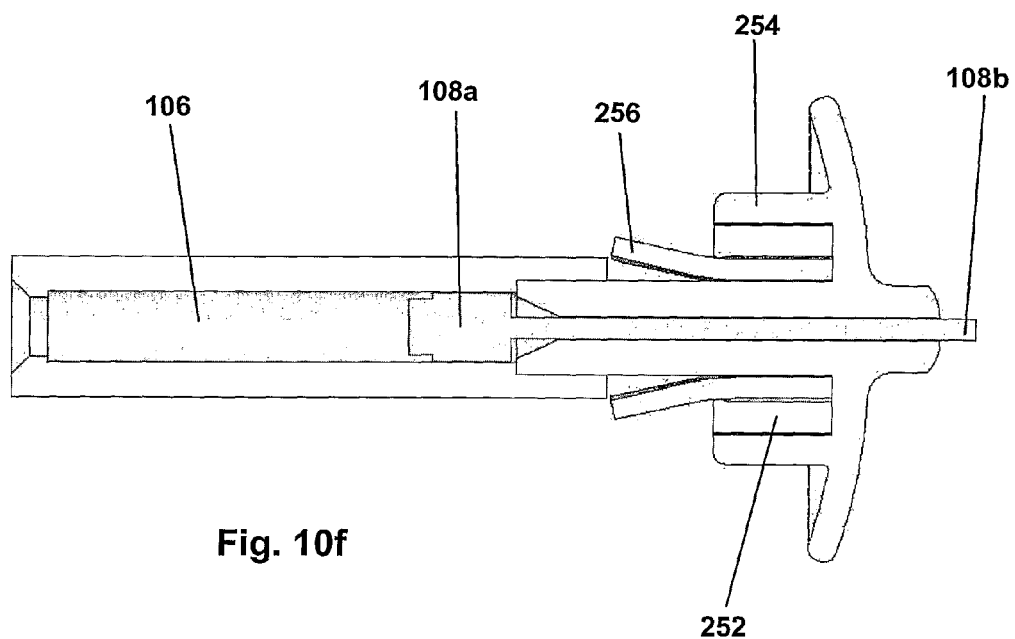
FIG. 10f is a cross sectional side view of the assembly of 10b taken along a longitudinal axis thereof and showing internal components of the assembly.
Figure 10G:
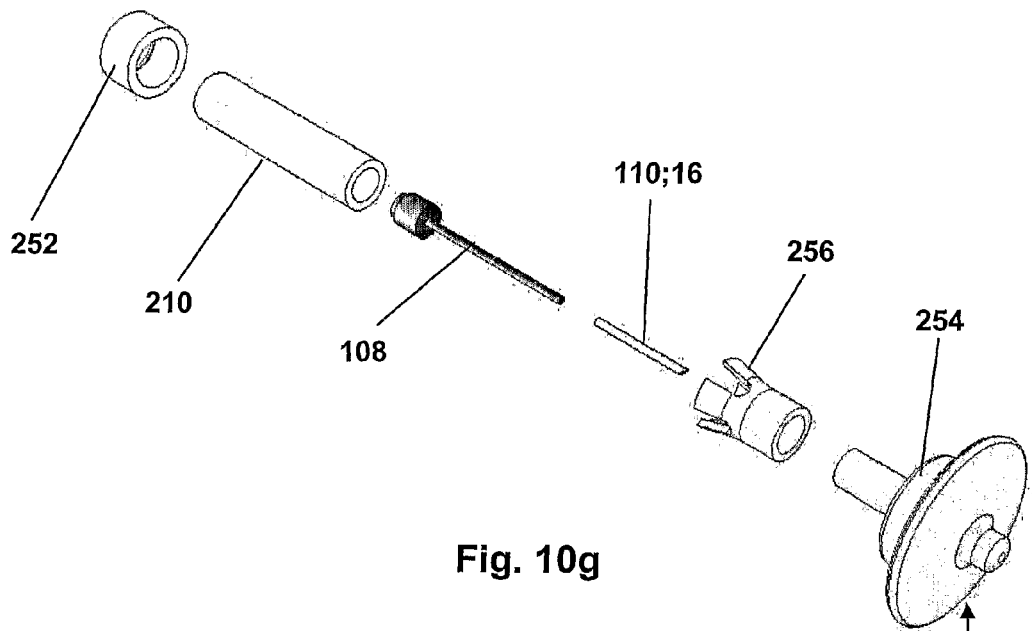
Figure 10H:
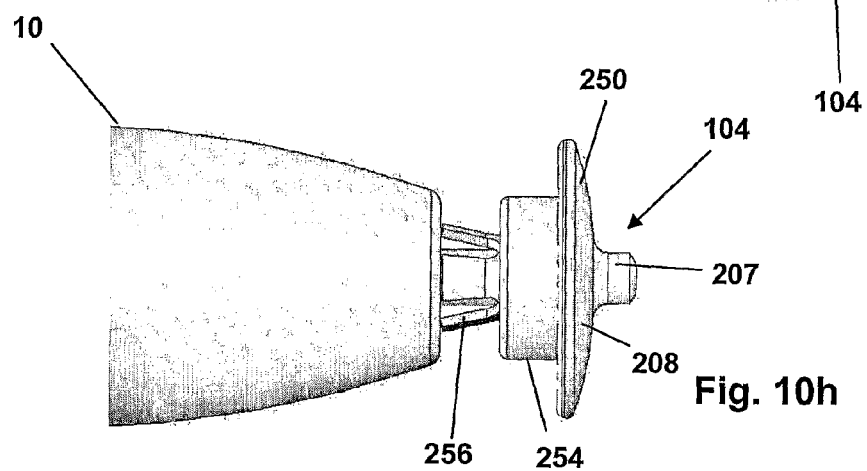
FIG. 10h is a side view of the assembly of FIG. 10b connected to the actuator device (shown in part), clearly showing the expanded wings restricting movement of the actuator device along the stem of the assembly.
Figure 10I:
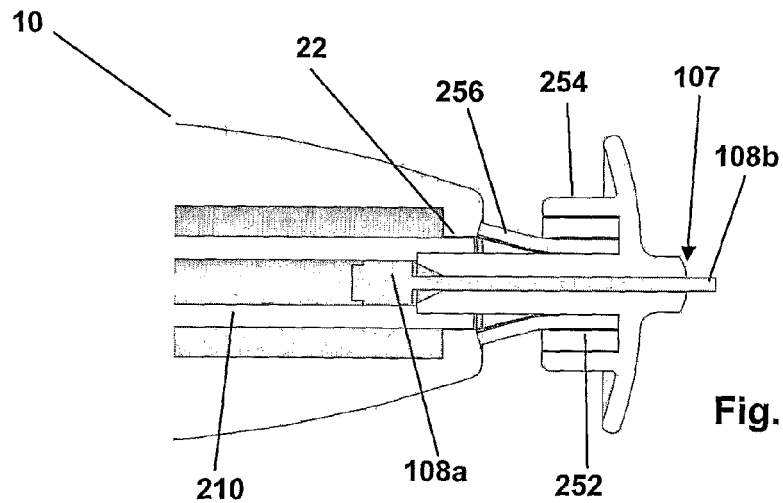
FIG. 10i is a cross sectional side view of the assembly and actuator device (shown in part) of FIG. 10h taken along a longitudinal axis thereof.
Figure 11A:
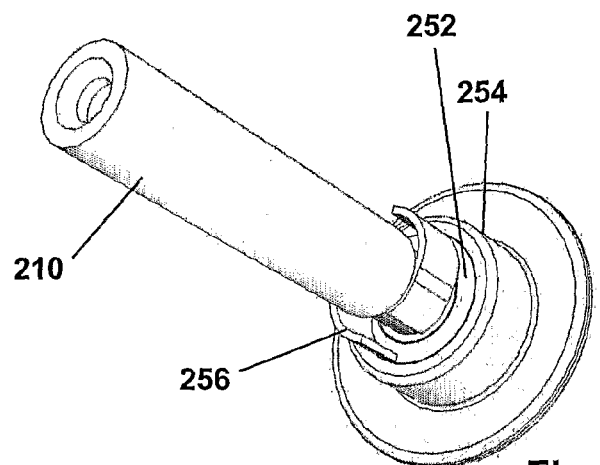
FIG. 11a is a perspective view of yet another embodiment of disposable assembly similar to that illustrated in FIGS. 10a to 10i showing an alternative shape of expandable wings, the assembly illustrated after actuation of the actuator device.
Figure 11B:
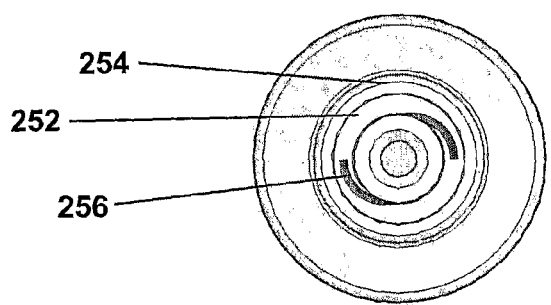
Figure 11C:
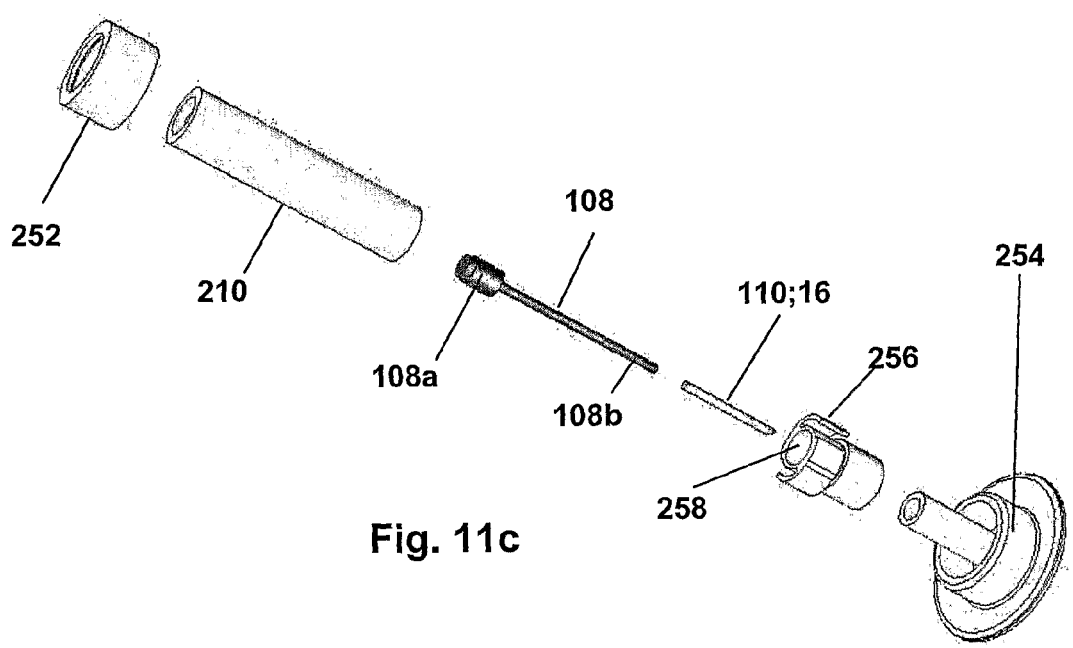
Figure 12D:
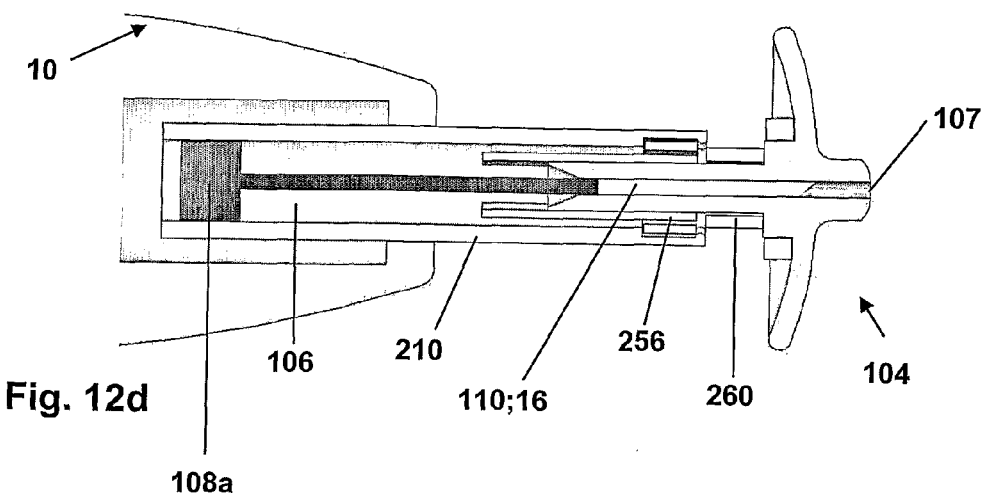
FIG. 12d is a cross sectional side view of the assembly and actuator device of FIG. 12a taken along a longitudinal axis thereof, showing internal components.
Figure 12E:
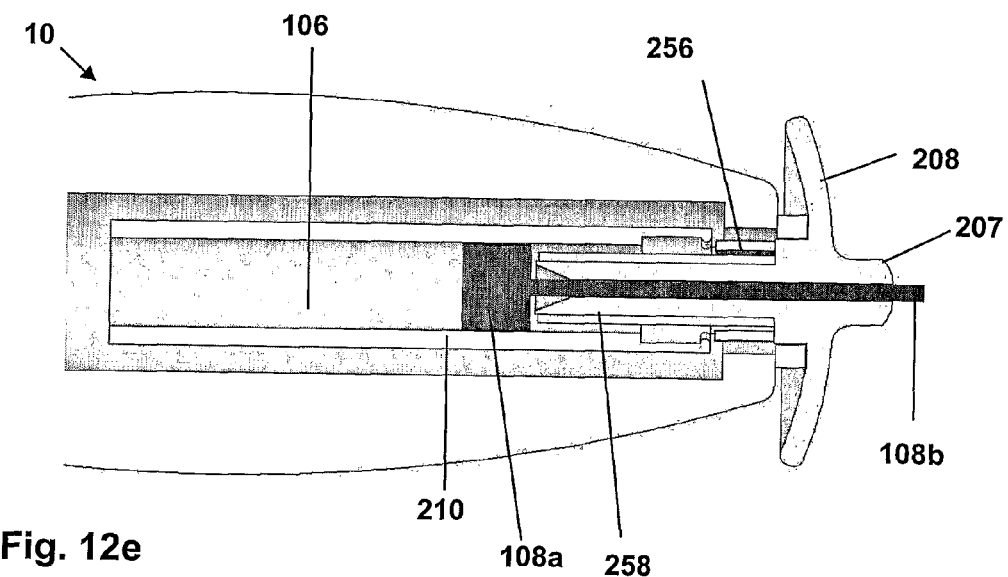
FIG. 12e is a cross sectional side view of the assembly and actuator device of FIG. 12a taken along a longitudinal axis thereof, showing internal components and the fully depressed position of the actuator device relative to the assembly on completing actuation of the actuator device.
Figure 12F:
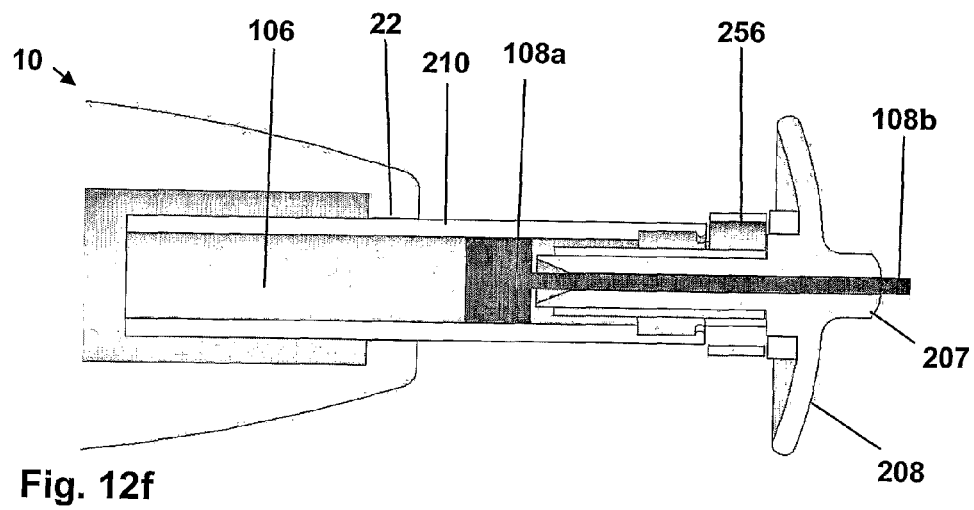
FIG. 12f is a cross sectional side view of the assembly and actuator device of FIG. 12a taken along a longitudinal axis thereof, showing internal components and the expanded wings clearly protruding from the apertures in the stem wall after actuation of the actuator device and showing the fully retracted position of the actuator device along the stem when the actuation cycle has been completed.
Figure 13G:
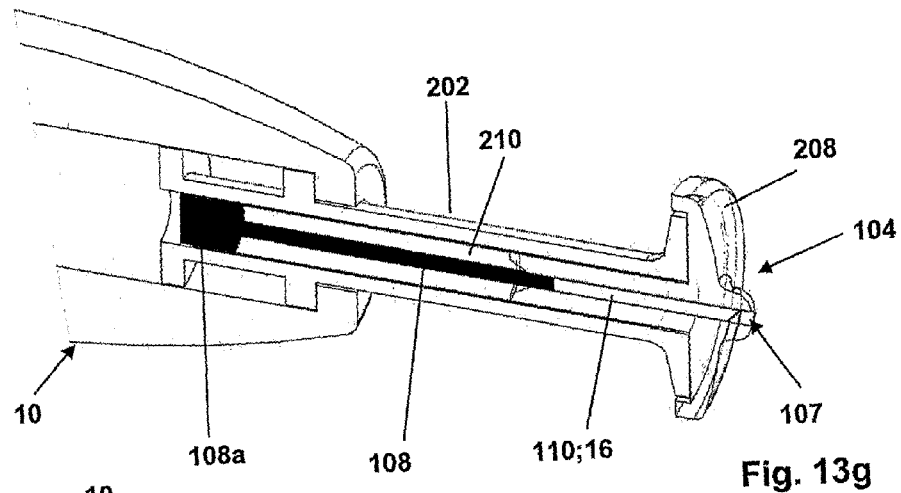
FIG. 13g is a perspective view of the assembly and actuator device of FIG. 13f shown here in cross section taken along a longitudinal axis of the assembly and actuator device, illustrating the un-crumpled cardboard covering and the position of internal components prior to actuation of the actuator device.
Figure 13H:
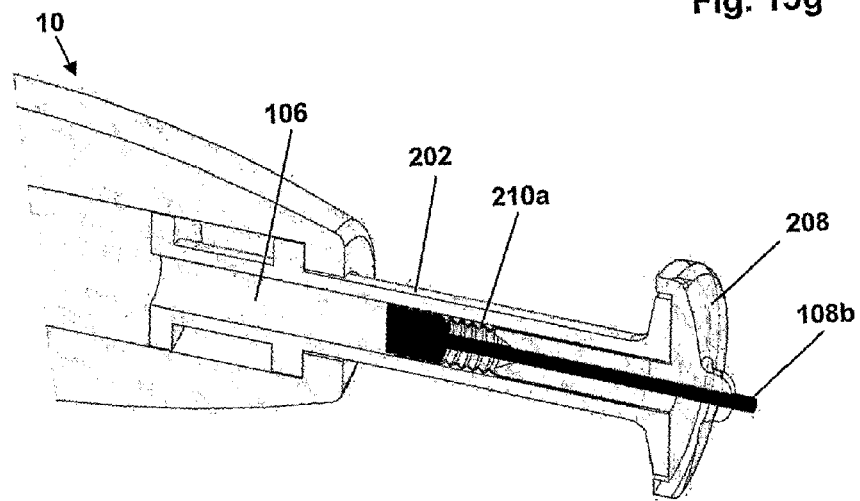
FIG. 13h is a similar view of the assembly and actuator device of FIG. 13g shown after an actuation cycle has been completed and the resulting crumpled portion of the weakened or pre-folded portion of the cardboard covering.
Figure 13I:
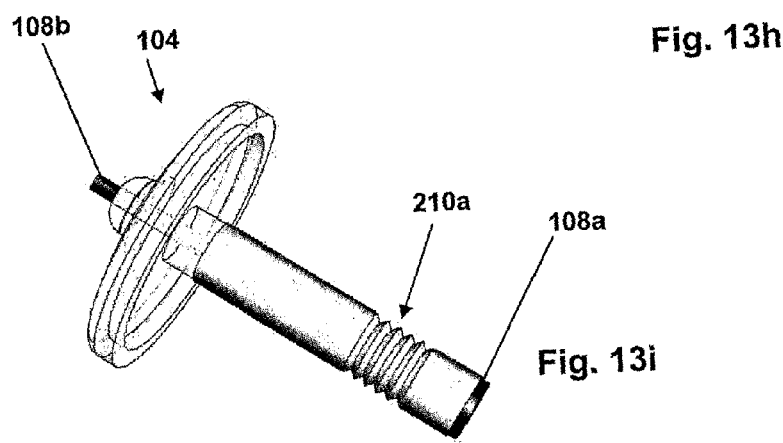

Referring initially to FIG. 10a which illustrates the assembly 200 prior to actuation of the actuator device 10, there is shown a two tiered collar system 251 located at the leading end of the stem 210 adjacent the skin contacting component 104. The two tiered collar system 251 comprises a first ring collar 252, which is slidable within a larger diametered second ring collar 254 which is fixed to the mushroom shaped skin contacting component 104. The diameter of each first and second ring collars 252, 254 is greater than the diameter of the stem 210.

During actuation of the assembly 200 and actuator device 10, the actuator device 10 slides along the stem 210 and impacts the first ring collar 252 sliding it within the second ring collar 254. After actuation of the actuator device 10, and as the actuator device 10 slides back along the stem 210 to its original position, it exposes resilient wings 256 which were first covered and restrained by the first ring collar 252 prior to actuation of the actuator device 10 and subsequently restrained by an inner wall of the actuator device 10 on actuation. Without the restraining effect of the first ring collar 252 or actuator 10, the wings 256 flare towards the trailing end of the assembly 200. This is shown most clearly in FIGS. 10d and 10f.

If actuation of the actuator device 10 is attempted for a second time, the flared wings 256 act as stop members preventing the actuator 10 sliding along the length of the stem 210 to actuate, thus disabling the assembly 200. This is shown most clearly in FIGS. 10h and 10i.

The flared wings 256 also make it visually clear to a user that the assembly 200 has already been used and thus the user will dispose of the used assembly 200 appropriately and replace it with an unused assembly 200. In this way, the disabling mechanism may also act as an indicating mechanism.

FIGS. 11a to 11e illustrate a similar disabling and indicating mechanism 240 as described above and illustrated in FIGS. 10a to 10i. In this embodiment, the wings 256 describe an S shaped configuration when viewed in the direction along the longitudinal axis of the stem 210.

FIGS. 12a to 12i illustrate another disabling and indicating mechanism 240 similar to that described above and illustrated by FIGS. 10a to 10i. In this embodiment, the resilient wings 256, which are similar in configuration to those described above and illustrated by FIGS. 10a to 10i are attached to and folded about a cylindrical shaped member 258 which sits within the stem 210 remote from the skin contacting component 104 prior to actuation of the actuator device 10. The wings 256 are restrained in the folded position by the inner wall of the stem 210.

During actuation, motion of the drive pin 108, by the actuator device 10, slides the cylindrical shaped member 258 along the length of the stem 210 until the cylindrical member 258 reaches and enters the apertures 260 in the wall of the stem 210 adjacent the skin contacting component 204. At this stage, an inner wall of the actuator device 10 restrains the wings 256 in their folded position.

After actuation of the actuator device 10, the actuator slides back along the stem 210 to its original position. The cylindrical member 258 is prevented from sliding back along the stem because the wings are held in the apertures 260. After the actuator device 10 clears the apertures 260, the resilient wings 256 are exposed and without the restraining effect of the inner wall of the stem 210 or actuator device 10, the wings 256 extend through the apertures 260 in the stem wall 210 of the assembly 200.

If actuation is attempted for a second time, the extended wings 256 act as stop members preventing the actuator 10 sliding along the length of the stem 210 to actuate, thus disabling the assembly 200. This is shown most clearly in FIGS. 12c and 12f.

The extended wings 256 also make it visually clear to a user that the assembly 200 has already been used and thus the user will dispose of the used assembly 200 appropriately and replace it with an unused assembly 200. In this way, the disabling mechanism may also act as an indicating mechanism.

Figure 15A:
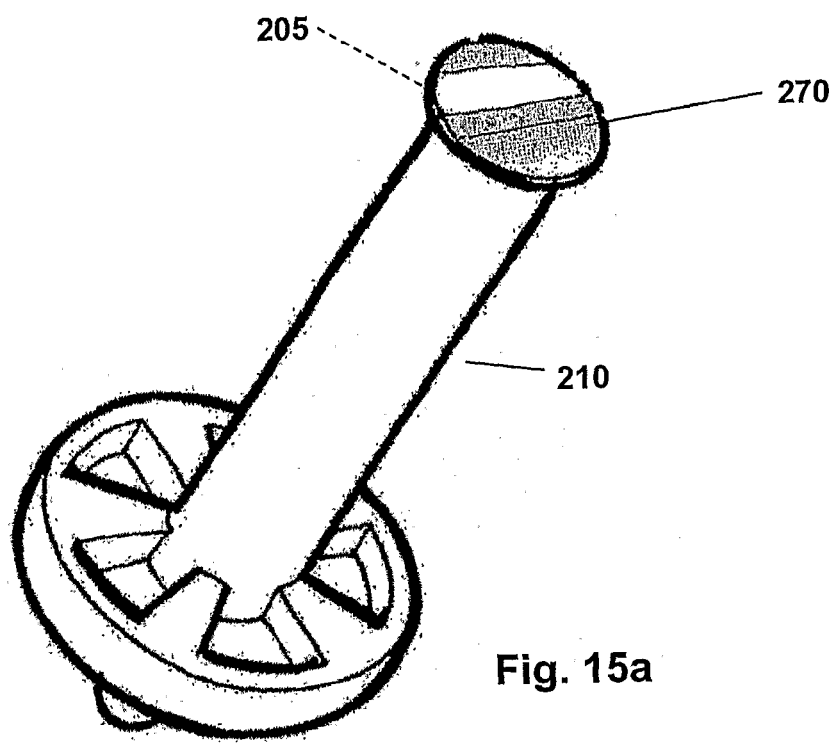
FIG. 15a is a perspective view and from the trailing end of an embodiment of disposable assembly illustrating an alternative indicating mechanism in the form of a rupturable foil covering an open end of the stem at the trailing end of the assembly and which receives the actuator device, the foil being ruptured by the actuator device on insertion of the assembly therein.
Figure 15B:
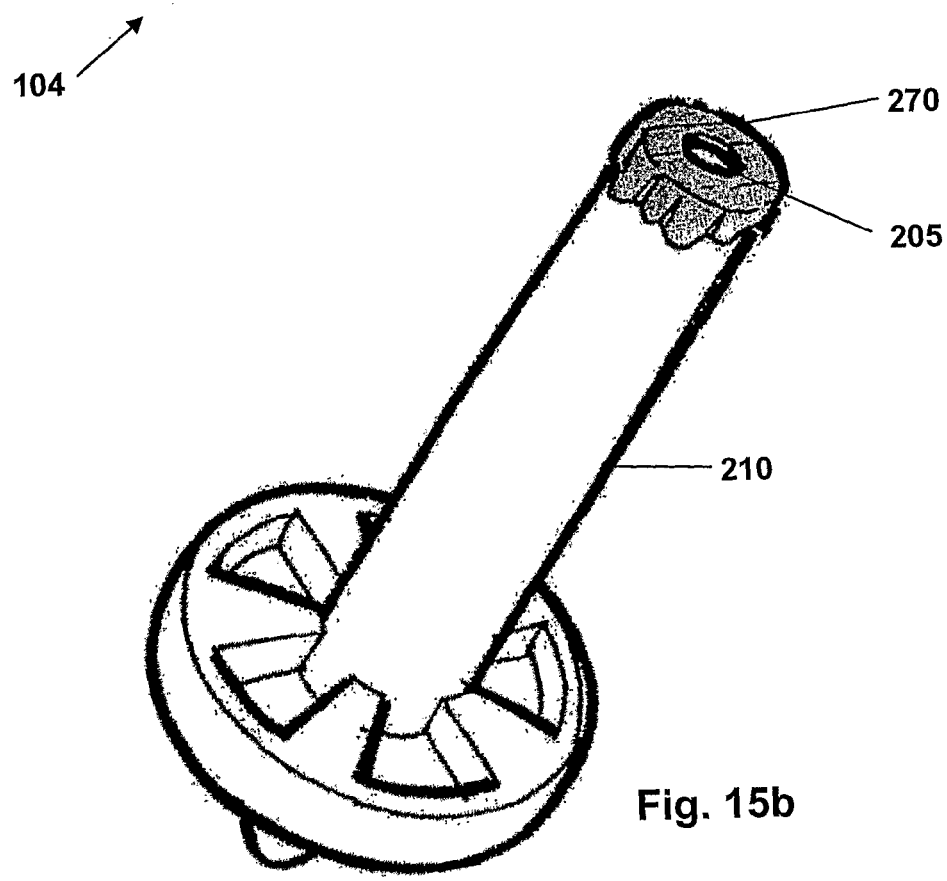
FIG. 15b is a perspective view of the assembly of FIG. 15a showing the foil ruptured after actuation of the actuator device.
Figure 16A:
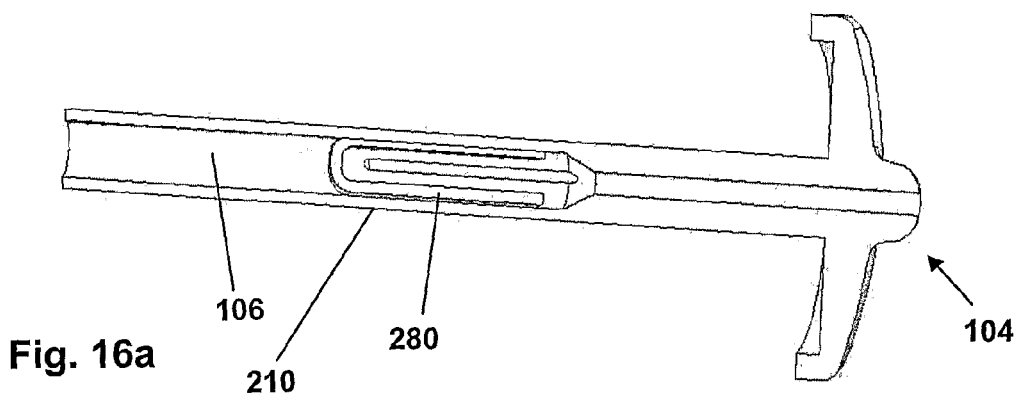
FIG. 16a is a cross sectional side view of a further embodiment of disposable assembly taken along a longitudinal axis thereof illustrating a further alternative disabling mechanism in the form of an expandable U-shaped member and its position within the channel of the assembly before actuation of the actuator device.
Figure 16B:
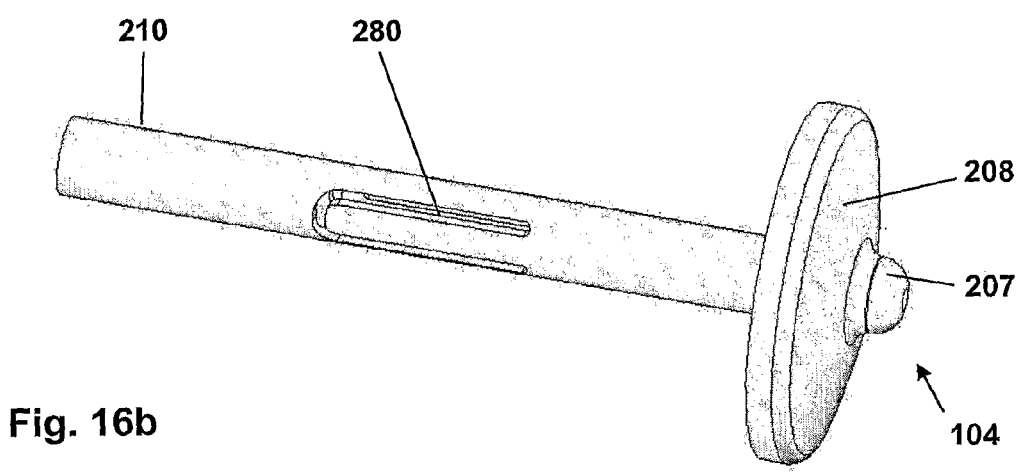
FIG. 16b is a perspective view of the assembly of FIG. 16b showing the hidden detail of the U-shaped member.
Figure 16C:
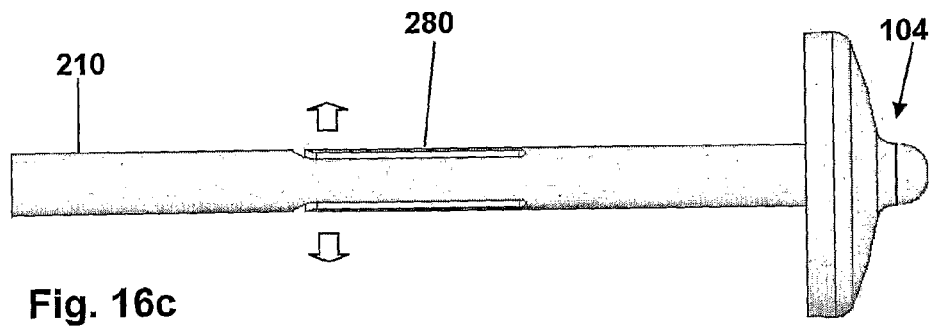
FIG. 16c is a side view of the assembly of FIG. 16a showing the direction of expansion of the U-shaped member after actuation of the actuator device.
Figure 16D:
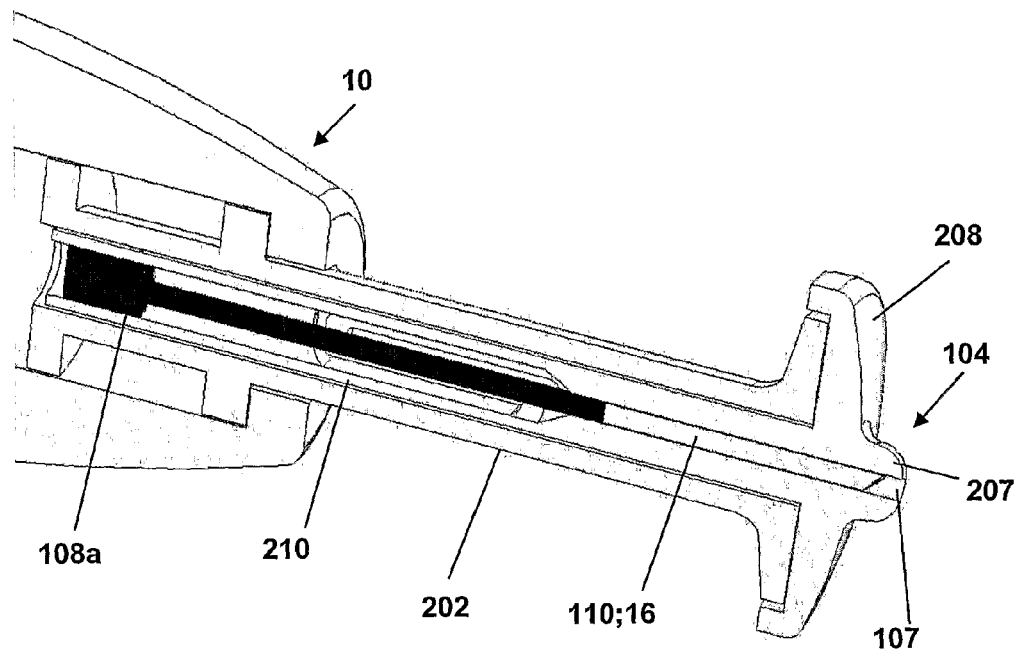
FIG. 16d is a perspective view of the assembly of FIG. 16a and actuator device of FIG. 13d (illustrated in part) shown here in cross section taken along a longitudinal axis of the assembly and actuator device, illustrating the position of internal components prior to actuation of the actuator device.
Figure 16E:
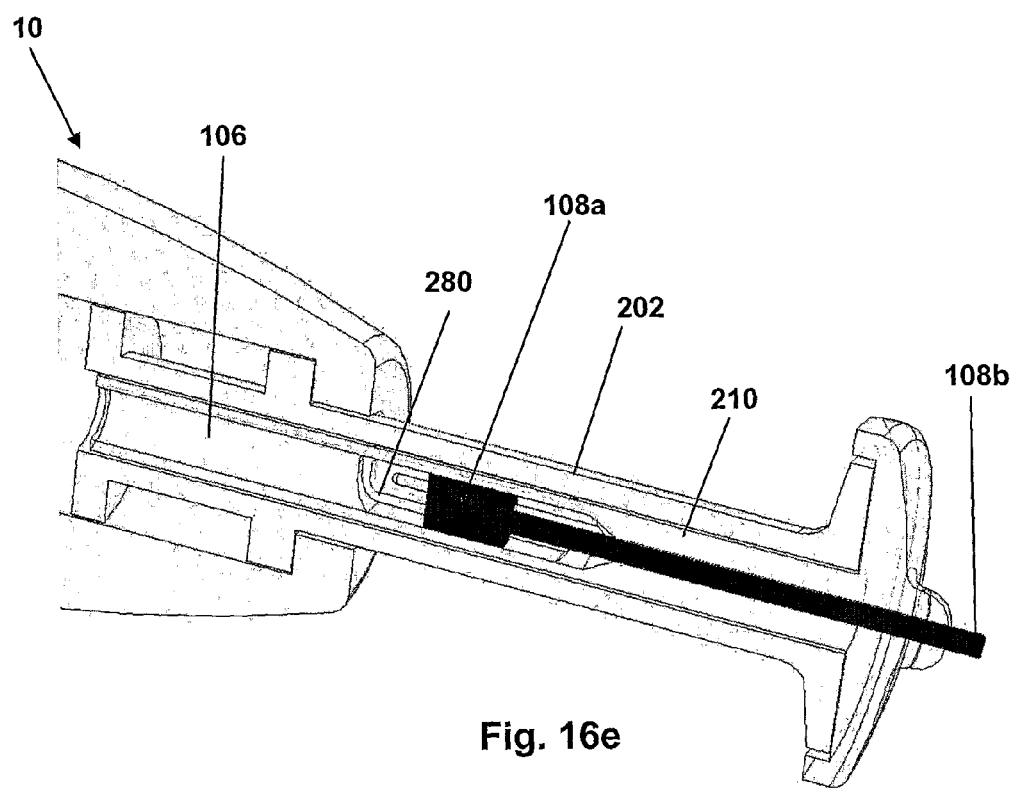
FIG. 16e is a view similar to FIG. 16d, illustrating the position of internal components and the actuator device after completing an actuation cycle.

Referring to FIGS. 13 to 15, there are illustrated further embodiments of disposable assembly 200 showing alternative indicating mechanisms 240.

In the embodiment exemplified in FIGS. 13a to 13i, the indicating mechanism 240 is a cylindrical cardboard section which forms the stem 210 of the assembly. The cardboard section 210 has a weakened or pre-folded portion 210a indicated by the dashed lines and which crumples on engagement with the moving drive pin 108 during actuation of the actuator device 10. This is shown most clearly in FIG. 13h. On removal of the assembly 200 after actuation the stem 210 is crumpled along the weakened portion 210a, thus clearly illustrating that the assembly 200 has been used.

In this embodiment, the actuator has a disposable elongate cylindrical portion 202 for receiving the assembly 200. This not only helps protect the weakened stem 210 but may also be disposed of after actuation preventing cross contamination of the actuator device with other disposable assemblies 200.

In FIG. 14a, a cardboard cover surrounds the stem 210 of the assembly 200 and crumples completely on engagement with the actuator device during actuation, thus visually illustrating when the assembly has been used, the assembly shown here prior to actuation.

The assembly 200 is also embossed along a length of the outer wall of the stem 210 with a fluorescent "used" sign which is revealed when the cardboard cover is crumpled, thus further aiding visual recognition that the assembly has been used.

FIG. 15a illustrates the use of a frangible seal 270 covering the stem opening 205. On insertion of the assembly 200 into the actuator device 10, the hammer 10 punctures the seal 270. After actuation and removal of the assembly 200 from the actuator device 10, the punctured seal 270 is a clear visual indication that the assembly has been used.

Referring to FIGS. 16a to 16e, there is illustrated a further embodiment of disposable assembly 200 showing an alternative disabling mechanism 240.

In this embodiment, the stem 210 is made of a deformable material, for example, cardboard. In a similar fashion to the embodiment described in FIGS. 13a to 13i, a disposable elongate cylindrical portion 202 for receiving the assembly 200. This not only helps protect the weaker walled stem 210 but may also be disposed of after actuation preventing cross contamination of the actuator device 10 with other disposable assemblies 200.

During actuation of the assembly 200 and actuator device 10, the drive pin 108 impacts a flexible, generally unshaped arm 280 located in the channel 106 causing it to expand. After withdrawal of the assembly 200 from the cylindrical portion 202, the expanded flexible arm 280 expands a portion of the weaker walled stem 210 in immediate contact therewith radially outwardly. This enlargens the diameter of the stem 210 at this expanded portion preventing re-insertion of the assembly 200 into the elongate cylindrical portion 202.

It will be appreciated that the invention is not limited to the embodiments hereinbefore described but may be varied in both construction and detail within the scope of the appended claims.

Furthermore, the skilled reader will appreciate that the principles described may be applied to generate alternative embodiments and these form part of the invention. In particular, it is possible to combine any of the aspects described in the above described embodiments.

It will be further appreciated that the assembly 200 of the present invention may be used in other areas of technology where it is required to penetrate a substrate or skin with a piercing element. For example, it is envisaged that the assembly 200 may be used with a suitable actuator in the construction industry. In this case, the skin or substrate may be concrete, wood or steel, and the skin piercing element may be a nail. Whilst the skin contacting component may be made redundant in this specific area of technology, the indicating and disabling mechanisms would operate in a similar fashion.

The invention claimed is:

1. An assembly in combination with a mechanical actuator device therefore, the assembly comprising:
    a housing having a proximal end and a distal end, the housing further having an opening to allow operative connection to the mechanical actuator device, a stem for engaging the mechanical actuator device and a channel within the stem, said channel containing:
    a skin piercing element that, prior to actuation of the mechanical actuator device, is positioned inside the housing such that it is unable to penetrate the skin and, upon actuation of the mechanical actuator device the skin piercing element is, at least in part, displaced from the distal end of the housing to penetrate the skin; and
    a drive pin or needle shaft in communication with the mechanical actuator device and the skin piercing element; and
    an indicating mechanism that signals when the assembly has been used; the indicating mechanism being visible on the stem; and
    wherein the opening is located at the proximal end of the housing; and
    wherein the indicating mechanism is located on the drive pin or needle shaft and, wherein the mechanical actuator device comprises a driving means for displacing the skin piercing element from the distal end of the housing upon actuation of the mechanical actuator device.

2. The combination as claimed in claim 1, wherein the stem defines at least a portion of the channel.

3. The combination as claimed in claim 1, wherein the skin piercing element is temporarily displaced from the end of the housing.

4. The combination as claimed in claim 1, wherein the assembly includes a resilient member located in the channel for retracting the skin piercing element or drive pin back into the housing after actuation of the mechanical actuator device.

5. The combination as claimed in claim 1, wherein the skin piercing element is a needle, or a plurality of needles.

6. The combination as claimed in claim 5, wherein the needle is a capillary needle, or a lancet, or a solid needle, or a tine needle.

7. The combination as claimed in claim 1, wherein the skin piercing element is a pioneer projectile or a drug splinter.

8. The combination as claimed in claim 1, wherein the indicating mechanism is combined with a disabling mechanism and the disabling mechanism comprises at least one actuatable member.

9. The combination as claimed in claim 8, wherein the at least one actuatable member extend in a lateral direction across the channel after actuation of the actuator device preventing a second actuation of the actuator device.

10. The combination as claimed in claim 9, wherein the at least one actuatable member extend outwardly of the stem wall to restrict the actuator device sliding along a length of the stem.

11. The combination as claimed in claim 9, wherein the at least one actuatable member extend inwardly of the stem wall to restrict movement of the skin piercing element or drive pin.

12. The combination as claimed in claim 8, wherein the at least one actuatable member are located on a shaft of the skin piercing element or drive pin, which after actuation of the actuator device extends outwardly from the needle or drive pin to engage a stop member within the stem which prevents the needle or drive pin being withdrawn back into the assembly.

13. The combination as claimed in claim 8 wherein the disabling mechanism prevents the assembly from being re-used with the mechanical actuator device.

14. The combination as claimed in claim 1, wherein the indicating mechanism is a deformable member located along a length of the stem or across the channel, the deformable member engagable with the actuator device or drive pin on actuation of the actuator device.

15. The combination as claimed in claim 8, wherein the at least one actuatable member is hinged or sprung.

16. The combination as claimed in claim 1, wherein a disabling mechanism disables the assembly after first actuation of the actuator device such that despite further attempts of actuation of the actuator device, the skin piercing element is inactivated such that it cannot leave the end of the housing.

17. The combination as claimed in claim 16, wherein the disabling mechanism locks the skin piercing element within the channel.

18. The combination as claimed in claim 16, wherein the indicating and disabling mechanisms comprises a plurality of actuatable members.

19. The combination as claimed in claim 18, comprising a first actuatable member which is acted on by actuation of the mechanical actuator device and a second actuatable member which acts after actuation of the mechanical actuator device.

20. The combination as claimed in claim 19, wherein the second actuatable member comprises integral resilient arms.

21. The combination as claimed in claim 19, wherein the first actuatable member is a release plunger and the second actuatable member is a slide detent.

22. The combination as claimed in claim 18, wherein actuation of the second actuatable member causes all or a part of the stem to expand radially outwards from the channel.

23. The combination as claimed in claim 1, comprising a first and second actuatable members which form part of the stem and which are biased to move towards the channel.

24. The combination as claimed in claim 23, further comprising first and second channel bridging members which, prior to actuation of the actuator device, counter the first and second actuatable members.

25. The combination as claimed in claim 24, wherein the first and second channel bridging members are respectively a drive pin head and a ring member.

26. The combination as claimed in claim 1, wherein the assembly comprises a skin contacting component located at a leading end of the assembly remote from the mechanical actuator device.

27. The combination assembly as claimed in claim 26, wherein the skin contacting component has a primary skin tensioning surface.

28. The combination as claimed in claim 26, wherein the skin contacting component has a secondary skin tensioning surface located intermediate the primary skin tensioning surface and a trailing end of the assembly.

29. The combination as claimed in claim 1 wherein the indicator mechanism is visible through an aperture in the housing.

30. The combination as claimed in claim 1, wherein the assembly is disposable.

31. A combination as claimed in claim 30 wherein the mechanical actuator is reusable.

32. A single use combination device comprising a disposable assembly as claimed in claim 30.

33. An assembly for use with a mechanical actuator device, the assembly comprising:
  a housing having an opening to allow operative connection to the mechanical actuator device, an aperture and a stem for engaging the mechanical actuator device and a channel within the stem, said channel containing:
  a skin piercing element that, prior to actuation of the mechanical actuator device, is positioned inside the housing such that it is unable to penetrate the skin and, upon actuation of the mechanical actuator device the skin piercing element is, at least in part, displaced from an end of the housing to penetrate the skin; and
  a drive pin or needle shaft in communication with the mechanical actuator device and the skin piercing element; and
  an indicating mechanism located on the drive pin or needle shaft that signals when the assembly has been used; the indicating mechanism being visible on the stem; and
  wherein the indicating mechanism is combined with a disabling mechanism located on the needle shaft or drive pin, the disabling mechanism comprising at least one actuatable member that engages with the aperture to disable the assembly.

\* \* \* \* \*